(12) United States Patent
Gangjee

(10) Patent No.: US 10,538,527 B2
(45) Date of Patent: Jan. 21, 2020

(54) CYCLOPENTA[D]PYRIMIDINES AND SUBSTITUTED CYCLOPENTA[D]PYRIMIDINES AS ANTITUBULIN AND MICROTUBULE TARGETING AGENTS, MONOCYCLIC PYRIMIDINES AS TUBULIN INHIBITORS, AND PYRROLOPYRIMIDINES AS TARGETED ANTIFOLATES AND TUBULIN AND MULTIPLE RECEPTOR TYROSINE KINASE INHIBITION AND ANTITUMOR AGENTS

(71) Applicant: Duquesne University of the Holy Spirit, Pittsburgh, PA (US)

(72) Inventor: Aleem Gangjee, Allison Park, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

(21) Appl. No.: 16/266,928

(22) Filed: Feb. 4, 2019

(65) Prior Publication Data

US 2019/0241571 A1     Aug. 8, 2019

Related U.S. Application Data

(62) Division of application No. 15/130,219, filed on Apr. 15, 2016, now Pat. No. 10,239,880.

(60) Provisional application No. 62/149,038, filed on Apr. 17, 2015.

(51) Int. Cl.
*C07D 487/04* (2006.01)
*C07D 239/94* (2006.01)

(52) U.S. Cl.
CPC ......... *C07D 487/04* (2013.01); *C07D 239/94* (2013.01)

(58) Field of Classification Search
CPC ............................ C07D 487/04; C07D 239/94
See application file for complete search history.

(56) References Cited

U.S. PATENT DOCUMENTS

| 4,450,162 A * | 5/1984 | Kamioka | ............. C07D 239/70 514/256 |
|---|---|---|---|
| 2010/0129470 A1 | 5/2010 | Laughlin | |
| 2012/0264768 A1 | 10/2012 | Gangjee | |

FOREIGN PATENT DOCUMENTS

WO    WO-2009144632 A1 * 12/2009 ........... C07D 473/34

OTHER PUBLICATIONS

Aguado et al. J. Comb. Chem., vol. 11, 2009, pp. 210-212.*
Pubchem, Substance Record for SID 174493671 Create Date: Apr. 3, 2014. [retrieved on Jul. 27, 2016]. Retrieved from the Internet: <https://pubchem.ncbi.nlm.nih.gov/substance/174493671>. entire document.
Pubchem, Substance Record for SID 142414655 Create Date: Aug. 12, 2012. [retrieved on May 24, 2016]. Retrieved from the Internet: <https://pubchem.ncbi.nlm.nih.gov/substance/142414655>. entire document.
Pubchem, Substance Record for SID 104509905 Create Date: Feb. 18, 2011. [retrieved on May 24, 2016]. Retrieved from the Internet: <https://pubchem.ncbi.nlm.nih.gov/substance/104509905>. entire document.
International Search Report and Written Opinion dated Oct. 5, 2016 for PCT/US2016/027807 filed Apr. 15, 2016.
Gangjee et al., Pharm. Res., 2012, vol. 29, No. 11, pp. 3033-3039.
Da et al. J. Med. Chem., 2013, vol. 56, pp. 7382-7395.

* cited by examiner

*Primary Examiner* — Samira J Jean-Louis
(74) *Attorney, Agent, or Firm* — Buchanan Ingersoll & Rooney; Craig G. Cochenour, Esq.

(57) ABSTRACT

The present invention provides a compound of Formula II, and salts thereof, and a pharmaceutical composition comprising a compound of Formula II:

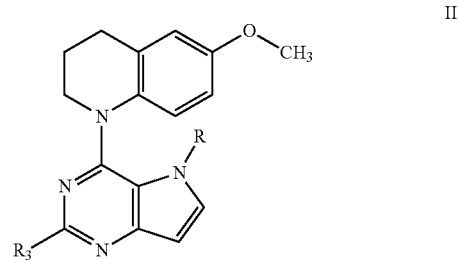

wherein R is hydrogen or an alkyl group having from one to ten carbon atoms, and wherein $R_3$ is hydrogen, an alkyl group having from one to ten carbon atoms, or a halogen. Preferably the compound of Formula II includes wherein $R_3$ is a halogen, and most preferably wherein the halogen is chlorine. Methods of treating a patient with cancer with these compounds are also provided.

7 Claims, 29 Drawing Sheets

MS/MS fragmentation
of M1(5) or M2(4)
Exact Mass 239.1422
Measured 239.1340

Arrows indicate treatment days

Arrows indicate treatment days

CYCLOPENTA[D]PYRIMIDINES AND SUBSTITUTED CYCLOPENTA[D]PYRIMIDINES AS ANTITUBULIN AND MICROTUBULE TARGETING AGENTS, MONOCYCLIC PYRIMIDINES AS TUBULIN INHIBITORS, AND PYRROLOPYRIMIDINES AS TARGETED ANTIFOLATES AND TUBULIN AND MULTIPLE RECEPTOR TYROSINE KINASE INHIBITION AND ANTITUMOR AGENTS

CROSS-REFERENCE TO RELATED APPLICATION

This is a divisional patent application that claims the benefit of co-pending U.S. patent application Ser. No. 15/130,219, filed Apr. 15, 2016, that claims the benefit of U.S. Patent Application Ser. No. 62/149,038, filed Apr. 17, 2015. The entire contents of U.S. patent application Ser. Nos. 15/130,219 and 62/149,038 are incorporated by reference into this divisional patent application as if fully written herein.

STATEMENT REGARDING FEDERALLY SPONSORED RESEARCH OR DEVELOPMENT

This invention was made with government support under Grant No. RO1 CA142868 awarded by the National Institute of Health, National Cancer Institute; and Grant Nos. CA 125153, CA152316, CA53535, CA166711, and GM094472 awarded by the National Institute of Health, National Cancer Institute. The government has certain rights in the invention.

BACKGROUND OF THE INVENTION

1. Field of the Invention

The present invention provides pyrimidine compounds having antitubulin and microtubule targeting agents, and targeted antifolates and tubulin and multiple receptor tyrosine kinase inhibition and antitumor agent activity.

2. Description of the Background Art

Combinations of targeted therapies and cytotoxic therapies are a mainstay of modern cancer therapy. Such combinations can provide advantages by addressing biological redundancy, attaining additive or synergistic mechanisms of drug action and targeting tumor heterogeneity.[1,6] Our longstanding interest has been to design single entities with both cytotoxic and targeted antiangiogenic effects.[7,8,9] Compared to combination chemotherapy, single agents that act on multiple targets could retain the advantages of drug combinations while potentially synchronizing the mechanisms of action and simplifying pharmacokinetic hurdles.

The present invention describe the preclinical studies of synthetic molecules with the ability to initiate microtubule depolymerization and inhibit receptor tyrosine kinases (RTKs). Microtubules play essential roles in cell biology facilitating both mitotic and non-mitotic processes. Agents that disrupt microtubule dynamics are some of the most successful agents in cancer therapy. The synthesized molecules were designed to bind the colchicine site on tubulin, similar to combretastatin A-4, one of several known tubulin binding sites that disrupt microtubule dynamics. Several RTKs initiate angiogenic events including the epidermal growth factor receptor (EGFR), vascular endothelial growth factor receptor 2 (VEGFR-2) and platelet-derived growth factor receptor β (PDGFR-β). Inhibitors of these RTKs are useful in combination with cytotoxic agents due to their ability to normalize surviving tumor vessels, which increases blood flow and cytotoxic drug delivery to the tumor.[1,2] Hence, a promising approach in combination therapy is to deliver the RTK inhibitor and the cytotoxic agent in a manner that facilitates this interaction, so as to have the best therapeutic advantage of the combination. The present invention provides compounds that have an advantage over other agents due to their intrinsic ability to synchronize these two drug mechanisms.

SUMMARY OF THE INVENTION

The present invention provides a compound of Formula I, and salts thereof:

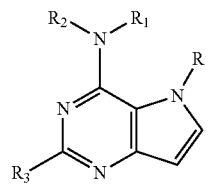

I wherein $R_1$ is selected from the group consisting of

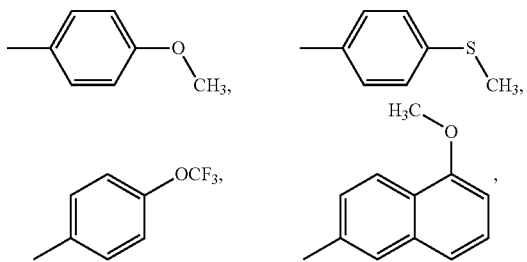

and $R_2$ is an alkyl group having from one to ten carbon atoms, or wherein $R_2$ is selected from the group consisting of

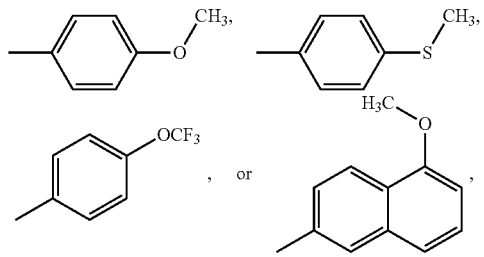

and
$R_1$ is an alkyl group having from one to ten carbon atoms; and R is H, or an alkyl group having from one to ten carbon atoms, and $R_3$ is H, an alkyl group having from one to ten carbon atoms, or a halogen. Preferably, the compound of Formula I, or salt thereof, includes wherein $R_1$ is selected from the group consisting of

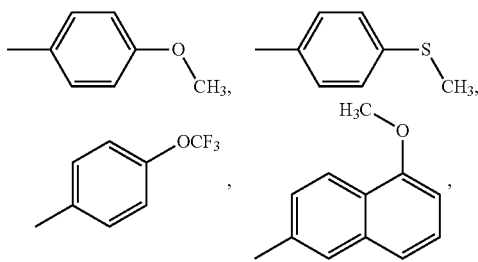

and R$_2$ is a methyl group, or wherein R$_2$ is selected from the group consisting of

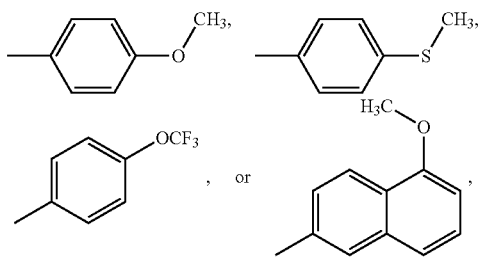

and R$_1$ is a methyl group; R$_3$ is a methyl group; and R is a hydrogen. More preferably, a compound is provided of Formula I, or a salt thereof, wherein R$_1$ is selected from the group consisting of

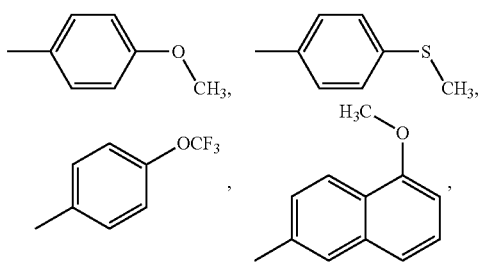

and R$_2$ is a methyl group, or
wherein R$_2$ is selected from the group consisting of

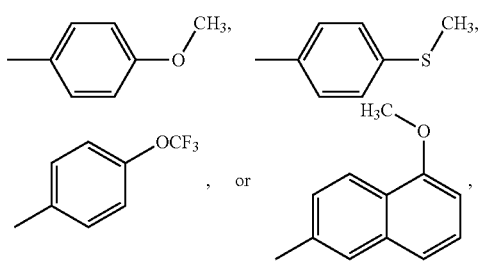

and R$_1$ is a methyl group; R$_3$ is a halogen; and R is a hydrogen. Most preferably, a compound is provided of Formula I, or salt thereof, wherein said halogen is a chlorine.

Another embodiment of this invention provides a compound of Formula I, or salt thereof, of Claim 1 wherein R$_2$ is

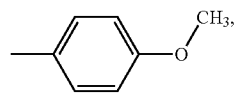

and R$_1$ and R$_3$ are each a methyl group, and R is a n-propyl group.

Another embodiment of this invention provides a compound of Formula I, or salt thereof, of Claim 1 wherein R$_1$ is

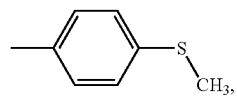

and R$_2$ is a methyl group; R$_3$ is a halogen; and R is a hydrogen. Preferably, this compound of Formula I, or salt thereof, includes wherein R$_3$ is a chlorine.

Another embodiment of this invention provides a compound of Formula I, or a salt thereof, of Claim 1 wherein wherein R$_1$ is

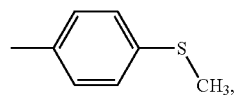

and R$_2$ is a methyl group; R$_3$ is a halogen; and R is a methyl group. Preferably, this compound of Formula I, or salt thereof, includes wherein R$_3$ is a chlorine.

In another embodiment of this invention, a pharmaceutical composition is provided comprising a compound of Formula I, and a pharmaceutically acceptable salt thereof:

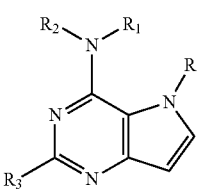

I wherein R$_1$ is selected from the group consisting of

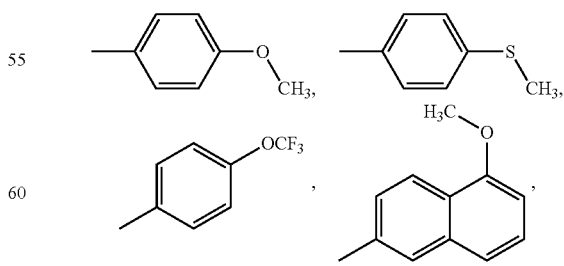

and R$_2$ is an alkyl group having from one to ten carbon atoms, or wherein R$_2$ is selected from the group consisting of

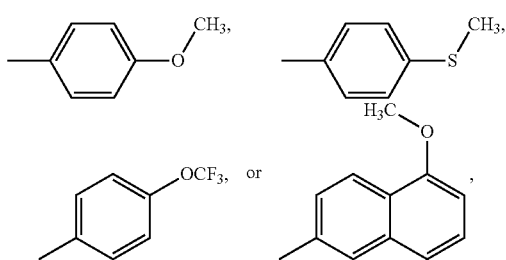

and
R$_1$ is an alkyl group having from one to ten carbon atoms; and R is H, or an alkyl group having from one to ten carbon atoms, and R$_3$ is H, an alkyl group having from one to ten carbon atoms, or a halogen.

Another embodiment of this invention provides a method of treating a patient having cancer comprising administering to a patient a therapeutically effective amount of a compound of Formula I, a salt of said compound of Formula I, or a pharmaceutical composition comprising a compound of Formula I to said patient for treating cancer, wherein

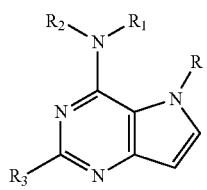

I wherein R$_1$ is selected from the group consisting of

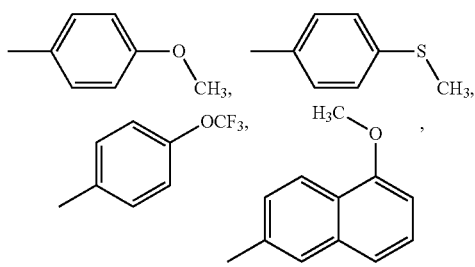

and R$_2$ is an alkyl group having from one to ten carbon atoms, or wherein R$_2$ is selected from the group consisting of

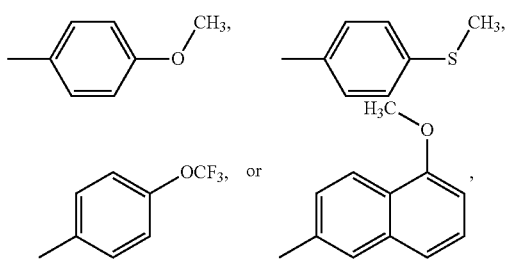

and
R$_1$ is an alkyl group having from one to ten carbon atoms; and R is H, or an alkyl group having from one to ten carbon atoms, and R$_3$ is H, an alkyl group having from one to ten carbon atoms, or a halogen. Preferably the halogen is chlorine.

Another embodiment of this invention provides a compound of Formula II, and salts thereof:

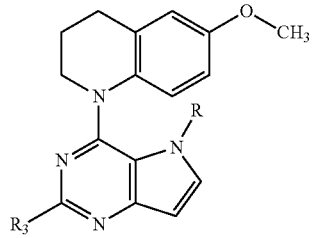

II wherein R is hydrogen or an alkyl group having from one to ten carbon atoms, and wherein R$_3$ is hydrogen, an alkyl group having from one to ten carbon atoms, or a halogen. Preferably, the compound of Formula II, and salt thereof, includes wherein the halogen is one selected from the group consisting of chlorine, bromine, fluorine, and iodine. More preferably, the compound of Formula II, and salt thereof, includes herein R is a hydrogen and R$_3$ is a halogen. Most preferably, the compound of Formula II, and salt thereof, includes wherein R$_3$ is a chlorine. In another preferred embodiment of this invention, a compound of Formula II, and salt thereof, includes wherein R is a methyl group and R$_3$ is a halogen, and more preferably wherein the compound of Formula II, and salt thereof, includes wherein R$_3$ is chlorine.

Another embodiment of this invention provides a pharmaceutical composition comprising a compound of Formula II and a pharmaceutically acceptable salt thereof:

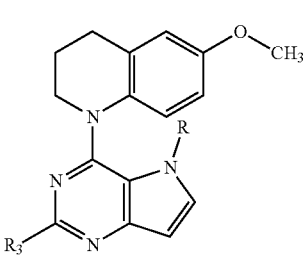

II wherein R is hydrogen or an alkyl group having from one to ten carbon atoms, and wherein R$_3$ is hydrogen, an alkyl group having from one to ten carbon atoms, or a halogen.

Another embodiment of this invention provides a method of treating a patient having cancer comprising administering to a patient a therapeutically effective amount of a compound of Formula II, a salt of said compound of Formula II, or a pharmaceutical composition comprising a compound of Formula II to said patient for treating cancer, wherein

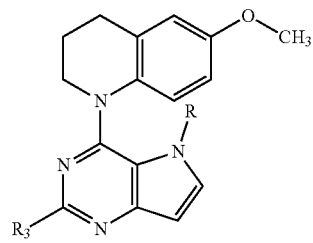

wherein R is hydrogen or an alkyl group having from one to ten carbon atoms, and wherein $R_3$ is hydrogen, an alkyl group having from one to ten carbon atoms, or a halogen.

Another embodiment of this invention provides a compound of Formula III, and salts thereof:

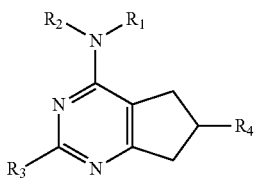

wherein $R_1$ is selected from the group consisting of:

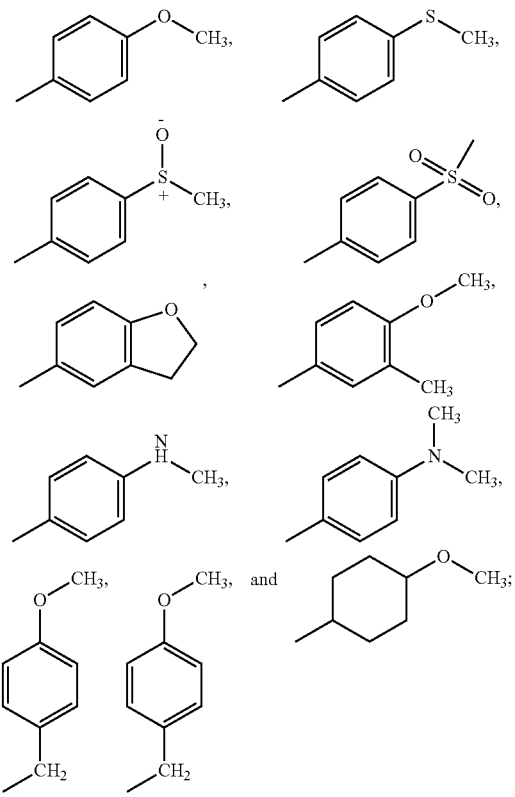

$R_2$ is H or an alkyl group having from one to ten carbon atoms; $R_3$ is H or an alkyl group having from one to ten carbon atoms; and $R_4$ is H or an alkyl group having from one to ten carbon atoms. Preferably, the compound of Formula III, and salts thereof, include wherein $R_3$ is a methyl group.

Another embodiment of this invention provides a pharmaceutical composition comprising a compound of Formula III and a pharmaceutically acceptable salt thereof:

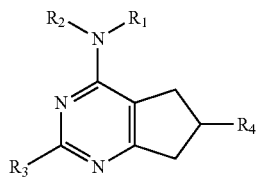

wherein $R_1$ is selected from the group consisting of:

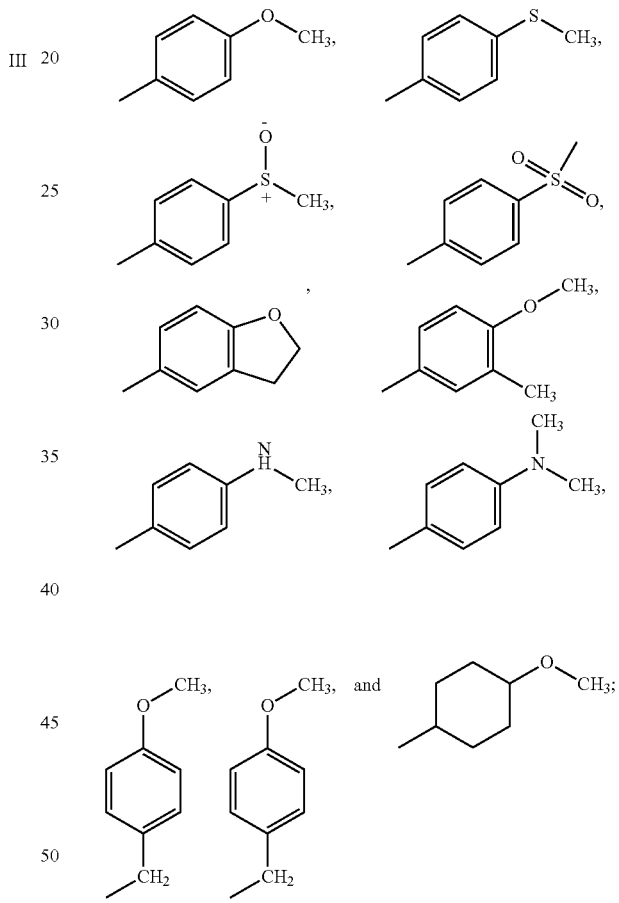

$R_2$ is H or an alkyl group having from one to ten carbon atoms; $R_3$ is H or an alkyl group having from one to ten carbon atoms; and $R_4$ is H or an alkyl group having from one to ten carbon atoms. Preferably, the pharmaceutical composition comprises a compound of Formula III wherein $R_3$ is a methyl group.

Another embodiment of this invention provides a method of treating a patient having cancer comprising administering to a patient a therapeutically effective amount of a compound of Formula III, a salt of said compound of Formula III, or a pharmaceutical composition comprising a compound of Formula III to said patient for treating cancer, wherein:

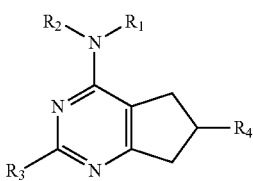

wherein $R_1$ is selected from the group consisting of:

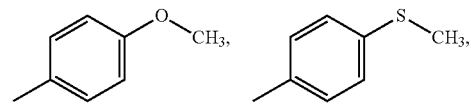

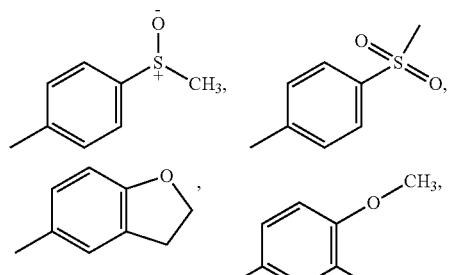

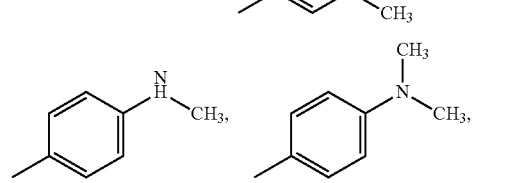

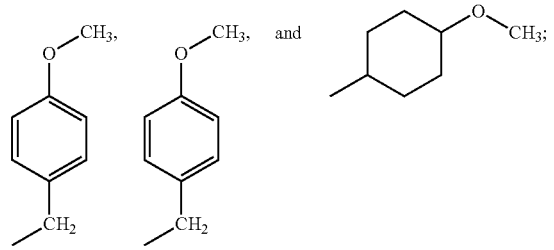

$R_2$ is H or an alkyl group having from one to ten carbon atoms; $R_3$ is H or an alkyl group having from one to ten carbon atoms; and $R_4$ is H or an alkyl group having from one to ten carbon atoms. Preferably, the method includes providing the pharmaceutical composition comprising a compound of Formula III wherein $R_3$ is a methyl group.

Another embodiment of this invention provides a compound of Formula IV, and a salt thereof:

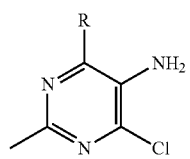

wherein R is one selected from the group consisting of:

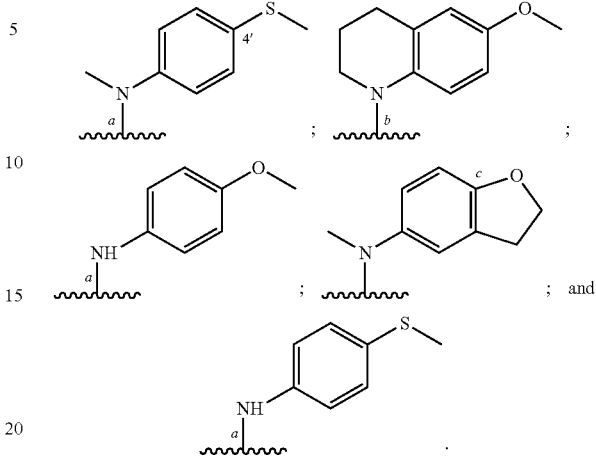

Another embodiment of this invention provides a pharmaceutical composition comprising a compound of Formula IV and a pharmaceutically acceptable salt thereof:

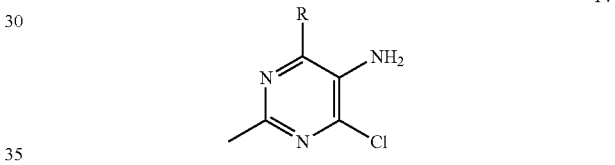

wherein R is one selected from the group consisting of:

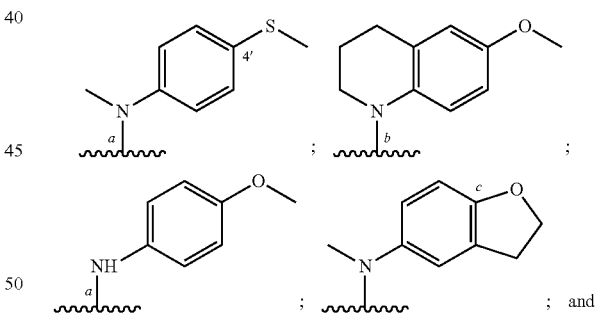

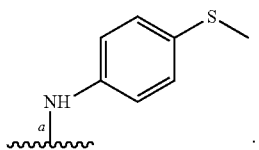

Another embodiment of this invention provides a method of treating a patient having cancer comprising administering to a patient a therapeutically effective amount of a compound of Formula IV, a salt of said compound of Formula IV, or a pharmaceutical composition comprising a compound of Formula IV to said patient for treating cancer, wherein:

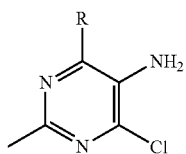

IV wherein R is one selected from the group consisting of:

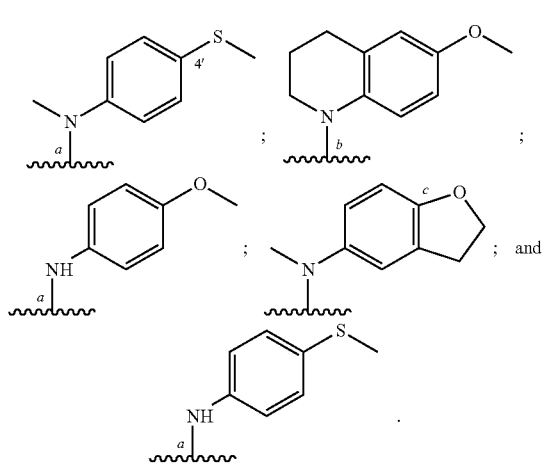

; and

Another embodiment of this invention provides a compound of Formula V, and a salt thereof:

FORMULA V

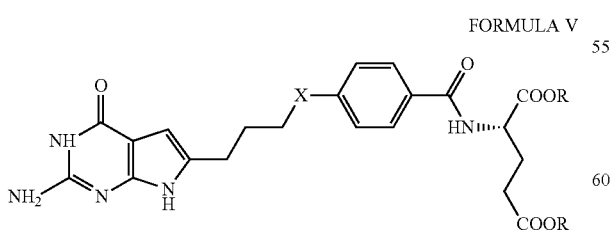

wherein X is selected from the group consisting of O, S, and NH, and wherein R is H or an alkyl group having from one to ten carbon atoms. Preferably, a compound of Formula V is provided wherein wherein X is S and R is H.

Another embodiment of this invention provides a pharmaceutical composition comprising a compound of Formula V and a pharmaceutically acceptable salt thereof:

FORMULA V

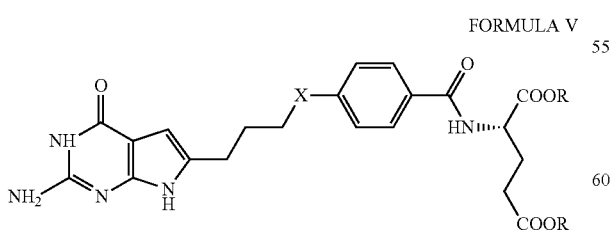

wherein X is selected from the group consisting of O, S, and NH, and wherein R is H or an alkyl group having from one to ten carbon atoms. Preferably, the pharmaceutical composition of Formula V includes wherein X is S and R is H.

Another embodiment of this invention provides a method of treating a patient having cancer comprising administering to a patient a therapeutically effective amount of a compound of Formula V, a salt of said compound of Formula V, or a pharmaceutical composition comprising a compound of Formula V to said patient for treating cancer, wherein:

FORMULA V

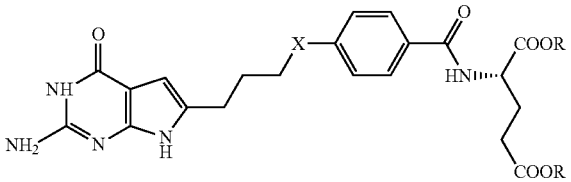

wherein X is selected from the group consisting of O, S, and NH, and wherein R is H or an alkyl group having from one to ten carbon atoms.

Another embodiment of this invention provides a compound of Formula VI, and salts thereof:

VI

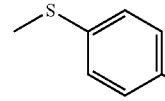

ZY/AG/145-626
(AG194)

Another embodiment of this invention provides a pharmaceutical composition comprising a compound of Formula VI and a pharmaceutically acceptable salt thereof:

VI

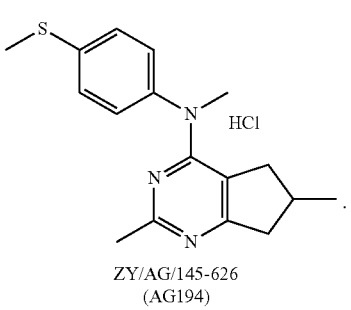

ZY/AG/145-626
(AG194)

Another embodiment of this invention provides a method of treating a patient having cancer comprising administering to a patient a therapeutically effective amount of a compound of Formula VI, a salt of said compound of Formula VI, or a pharmaceutical composition comprising a compound of Formula VI to said patient for treating cancer, wherein:

13

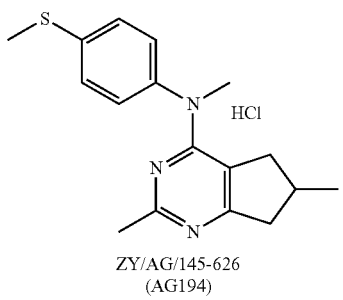

ZY/AG/145-626
(AG194)

Another embodiment provides a compound of Formula VII, and salts thereof:

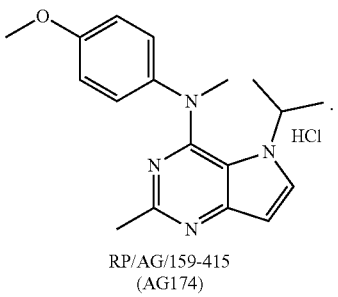

RP/AG/159-415
(AG174)

Another embodiment of this invention provides a pharmaceutical composition comprising a compound of Formula VI and a pharmaceutically acceptable salt thereof:

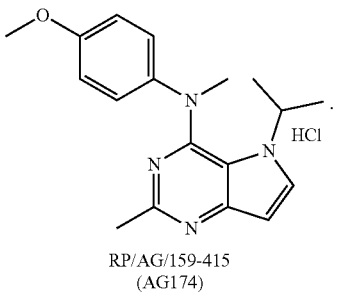

RP/AG/159-415
(AG174)

Another embodiment of this invention provides a method of treating a patient having cancer comprising administering to a patient a therapeutically effective amount of a compound of Formula VII, a salt of said compound of Formula VII, or a pharmaceutical composition comprising a compound of Formula VII to said patient for treating cancer, wherein:

14

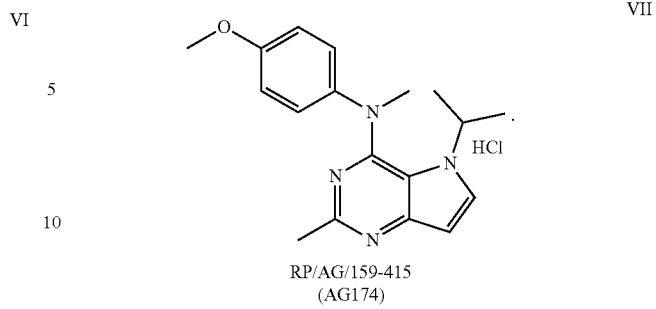

RP/AG/159-415
(AG174)

BRIEF DESCRIPTION OF THE DRAWINGS

A full understanding of the invention is gained from the following description of the preferred embodiments when read in conjunction with the accompanying drawings.

FIG. 7a) HPLC spectra of 3 incubated with human liver microsomes at 0 and 60 min. Metabolites M1-M5 and parent 3 were illustrated on the spectra. FIG. 7b) MS and MS/MS spectrum of 3. FIG. 7c) MS and MS/MS spectrum of M1 (compound 5). FIG. 7d) MS and MS/MS spectrum of M2 (compound 4). FIG. 7e) Fragmentation of M1 and M2 (MS/MS 239.1340).

DESCRIPTION OF THE PREFERRED EMBODIMENTS

Figure 1:
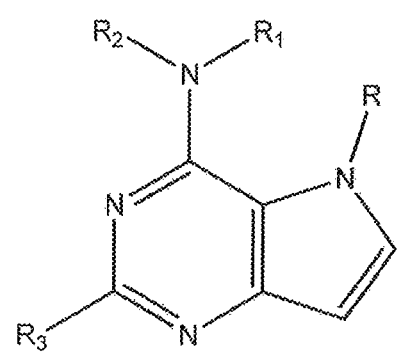
FIG. 1 shows the base structure of the compound of Formula I of this invention.

As used herein, the term "patient" means members of the animal kingdom, including but not limited to, human beings. As used herein "having cancer" means that the patient has been diagnosed with cancer.

As used herein, the term "therapeutically effective amount" refers to that amount of any of the present compounds of this invention that required to bring about a desired effect in a patient. The desired effect will vary depending on the illness being treated. For example, the desired effect may be reducing tumor size, destroying cancerous cells, and/or preventing metastasis, any one of which may be the desired therapeutic response. On its most basic level, a therapeutically effective amount is that amount needed to inhibit mitosis of a cancerous cell or to facilitate the reversal of multidrug resistance, particularly, for example, due to P-glycoprotein (i.e. an effective mitotic inhibitory amount). Any amount of mitotic inhibition or reversal of multidrug resistance will yield a benefit to a patient and is therefore within the scope of this invention.

As used herein, the term "alkyl having from one to ten carbon atoms" means, for example but not limited to, methyl, ethyl, propyl, butyl, pentyl, hexyl, cyclopropyl, cyclobutyl, cyclopentyl, and cyclohexyl groups. The alkyl groups may be straight, branched, or cyclic arrangements (cyclic arrangements are alkyl groups having from three to ten carbon atoms). The carbon atoms of these straight chain, branched chain, or cyclic arranged alkyl groups may have one or more substituents for the hydrogen(s) attached to the carbon atoms. The substituents may be the same or different and include, for example, moieties selected from the group consisting of straight, branched or cyclic alkyl, alkenyl or alkenyl, a cyclic or alicyclic group having from three to six carbon atoms, a heterocyclic group having from three to six carbon atoms, an alkoxy group, an aryloxy group, an alkyloxyaryloxy group, an aryl group, and an amine, a halogen, a phenol, a naphthalene, a piperidine, a pyrrole, a ketone, a methylalkylketone, and a trifluoromethyl ketone.

As used herein, the term "heteroalkyl" refers to alkyl chains from one to about ten atoms where one or more of the carbons has been replaced with nitrogen, oxygen or sulfur, Thus "heteroalkyl" groups will include, for example, —CH$_2$—CH$_2$—NH—, —CH$_2$—S—, —S—CH$_2$—, —CH$_2$—O—, —CH$_2$—CH$_2$—O—, —O—CH$_2$—, —NH—CH$_2$—CH$_2$—, —NH—CH=CH— and other various combinations, as will be apparent to one skilled in the art. The above list is not meant to be exhaustive, and many combinations are contemplated as within the scope of the present invention.

The term "aryl" groups, as used herein, refers to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl" refers to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" refers to ring systems in which one or more rings contain a heteroatom and one or more rings do not. It will be understood that this list is not meant to be exhaustive, and that any heteroaryl group, as these terms are defined above and commonly understood in the art, are within the scope of the present invention. The heteroaryl ring systems may be fused ring systems or unfused. Examples of heteroaryl ring systems include, for example but are are not limited to, pyridine, quinoline, isoquinoloine, pyrrole, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" refers to non-aromatic cyclic substituents in which one or more members of the ring is not carbon, for example oxygen, sulfur or nitrogen.

The terms "alkylaryl" (or "alkaryl") or "alkylheteroaryl" as used herein refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur, and therefore may be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and denotes attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about ten members. "Halogen"

refers to chlorine, bromine, iodine and fluorine. "Aryl and heteroaryl groups" are as described above. When a carboxylic acid is a substituent, it will be appreciated that the moiety represents an acid such as benzoic acid.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. As used herein, the term "glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described are contemplated as being within the scope of the present invention.

The present invention provides a compound of Formula I, and salts thereof:

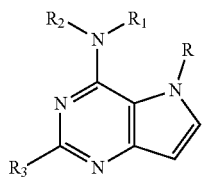

I wherein $R_1$ is selected from the group consisting of

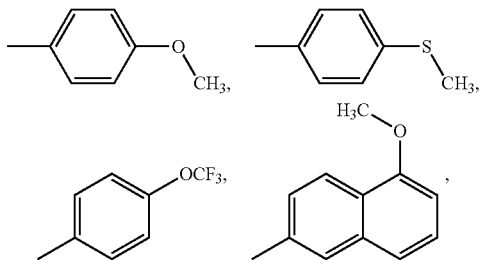

and $R_2$ is an alkyl group having from one to ten carbon atoms, or wherein $R_2$ is selected from the group consisting of

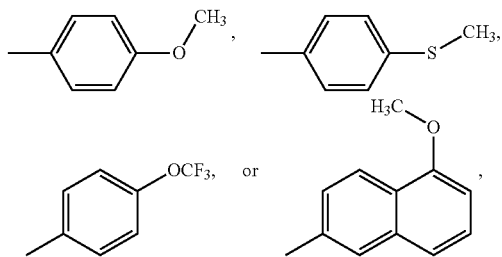

and
$R_1$ is an alkyl group having from one to ten carbon atoms; and

R is H, or an alkyl group having from one to ten carbon atoms, and $R_3$ is H, an alkyl group having from one to ten carbon atoms, or a halogen.

As used herein, the term "halogen" means an atom selected from the group consisting of chlorine, bromine, fluorine, and iodine.

In a preferred embodiment of this invention, a compound of Formula I, and salts thereof, is provided as set forth herein wherein $R_1$ is selected from the group consisting of

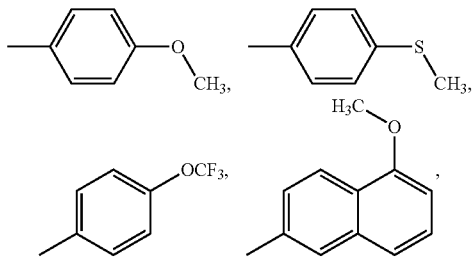

and $R_2$ is a methyl group, or
wherein $R_2$ is selected from the group consisting of

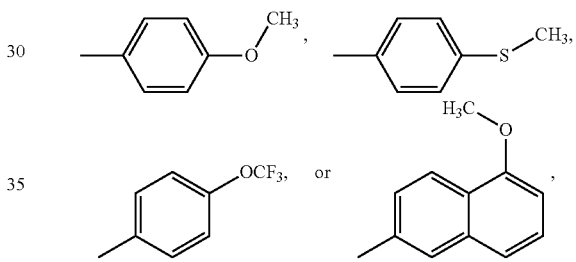

and $R_1$ is a methyl group; $R_3$ is a methyl group; and R is a hydrogen.

In another preferred embodiment of this invention, a compound of Formula I, and salts thereof, is provided as set forth herein wherein $R_1$ is selected from the group consisting of

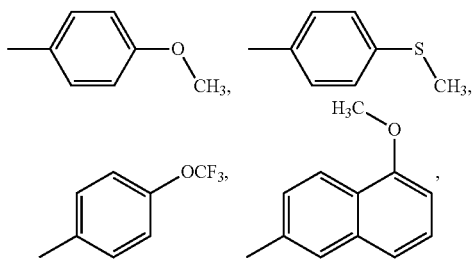

and $R_2$ is a methyl group, or
wherein $R_2$ is selected from the group consisting of

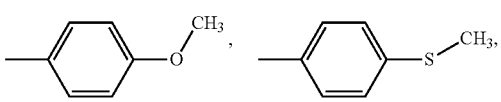

-continued

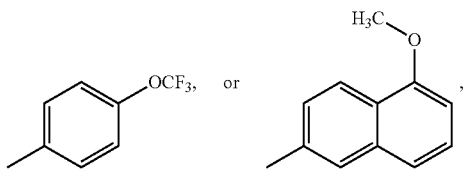

and $R_1$ is a methyl group; $R_3$ is a halogen; and R is a hydrogen. More preferably, this compound of Formula I is provided wherein the halogen is a chlorine.

In a preferred embodiment of this invention, a compound of Formula I, and salts thereof, is provided

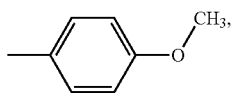
I wherein $R_2$ is

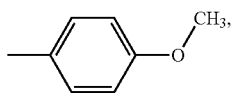

and $R_1$ and $R_3$ are each a methyl group, and R is a n-propyl group.

In another preferred embodiment of this invention, a compound of Formula I, and salts thereof, is provided as set forth herein wherein $R_1$ is

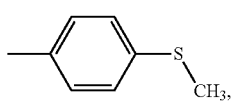

and $R_2$ is a methyl group; $R_3$ is a halogen; and R is a hydrogen. Most preferably, this compound of Formula I, and salts thereof, includes wherein $R_3$ is a chlorine.

In another preferred embodiment of this invention, a compound of Formula I, and salts thereof, is provided as set forth herein wherein $R_1$ is

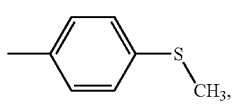

and $R_2$ is a methyl group; $R_3$ is a halogen; and R is a methyl group. Most preferably, this compound of Formula I, and salts thereof, includes wherein $R_3$ is a chlorine.

Another embodiment of this invention provides a pharmaceutical composition comprising a compound of Formula I, and a pharmaceutically acceptable salt thereof:

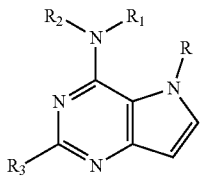
I wherein $R_1$ is selected from the group consisting of

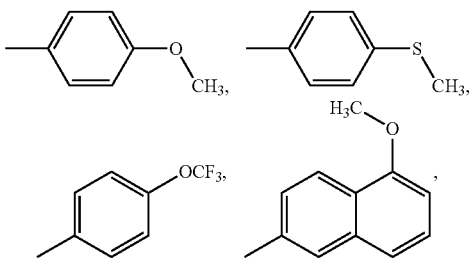

and $R_2$ is an alkyl group having from one to ten carbon atoms, or wherein $R_2$ is selected from the group consisting of

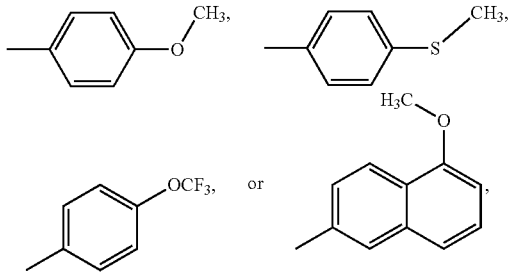

and
$R_1$ is an alkyl group having from one to ten carbon atoms; and
R is H, or an alkyl group having from one to ten carbon atoms, and
$R_3$ is H, an alkyl group having from one to ten carbon atoms, or a halogen.

In another embodiment of this invention, a compound of Formula II, and salts thereof, is provided:

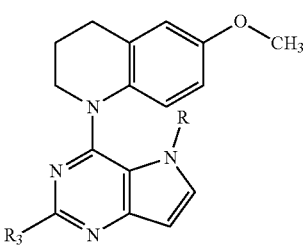
II wherein R is hydrogen or an alkyl group having from one to ten carbon atoms, and wherein $R_3$ is hydrogen, an alkyl group having from one to ten carbon atoms, or a halogen. More preferably, this compound of Formula II, and salts thereof, is provided wherein the halogen is a chlorine.

In a preferred embodiment of this invention, a compound of Formula II, and salts thereof, is provided

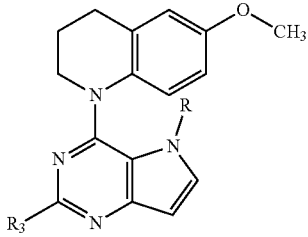

wherein R is a hydrogen and $R_3$ is a halogen. Most preferably, this compound of Formula II, and salts thereof, includes wherein R is a hydrogen and $R_3$ is a chlorine.

In another preferred embodiment of this invention, a compound of Formula II, and salts thereof, is provided

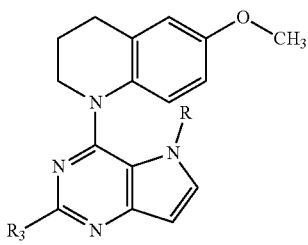

wherein R is a methyl group and $R_3$ is a halogen. Most preferably, this compound of Formula II, and salts thereof, includes wherein R is a methyl group and $R_3$ is chlorine.

Another embodiment of this invention provides a pharmaceutical composition comprising a compound of Formula II and a pharmaceutically acceptable salt thereof:

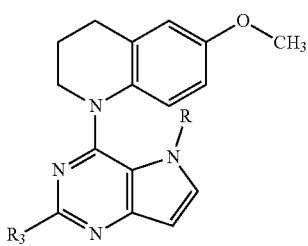

wherein R is hydrogen or an alkyl group having from one to ten carbon atoms, and wherein $R_3$ is hydrogen, an alkyl group having from one to ten carbon atoms, or a halogen.

Another embodiment of this invention provides for a compound of Formula III, and salts thereof:

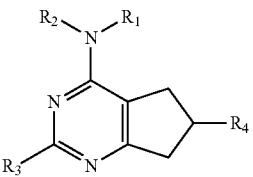

wherein $R_1$ is selected from the group consisting of:

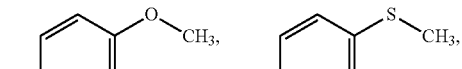
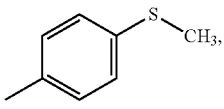
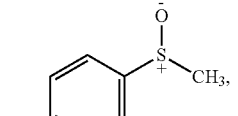
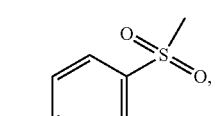
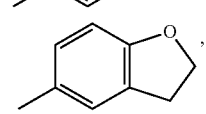
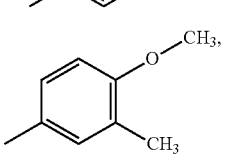
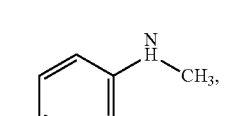
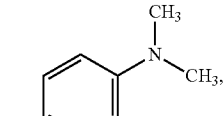
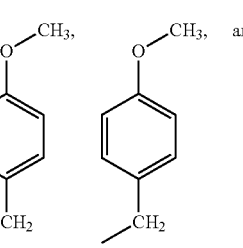
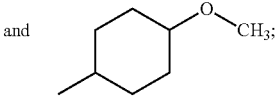

$R_2$ is H or an alkyl group having from one to ten carbon atoms; $R_3$ is H or an alkyl group having from one to ten carbon atoms; and $R_4$ is H or an alkyl group having from one to ten carbon atoms. Preferably, a compound having the structure of Formula III is provided wherein $R_3$ is a methyl group.

Another embodiment of this invention provides a pharmaceutical composition comprising a compound of Formula III and a pharmaceutically acceptable salt thereof:

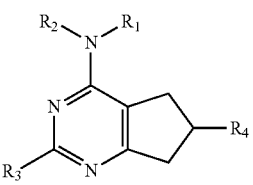

wherein $R_1$ is selected from the group consisting of:

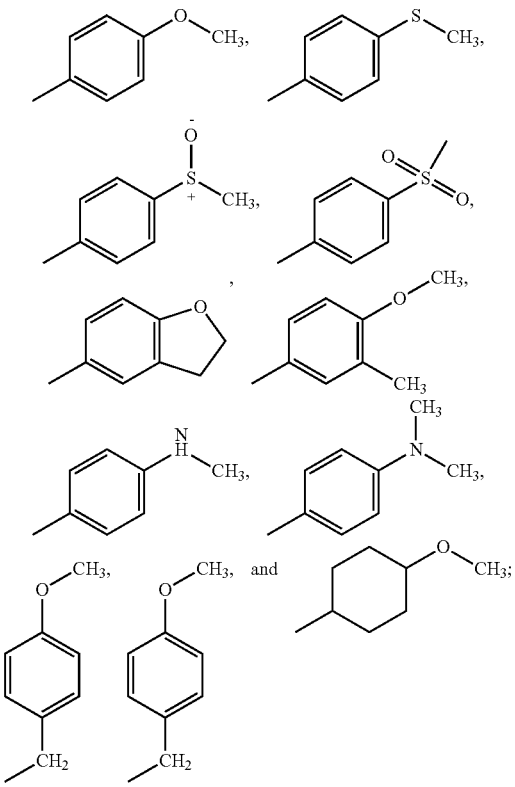

$R_2$ is H or an alkyl group having from one to ten carbon atoms; $R_3$ is H or an alkyl group having from one to ten carbon atoms; and $R_4$ is H or an alkyl group having from one to ten carbon atoms. Preferably, a pharmaceutical composition is provided comprising a compound having the structure of Formula III, as set forth herein, wherein $R_3$ is a methyl group.

Another embodiment of this invention provides a compound of Formula IV, and a salt thereof:

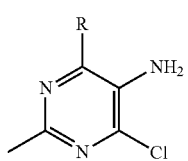

wherein R is one selected from the group consisting of:

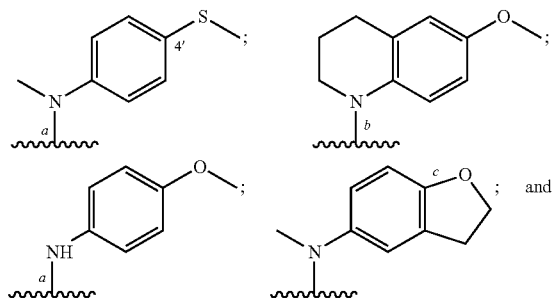

-continued

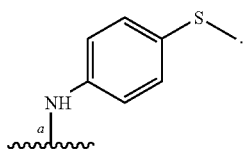

Another embodiment of this invention provides for a pharmaceutical composition comprising a compound of Formula IV and a pharmaceutically acceptable salt thereof:

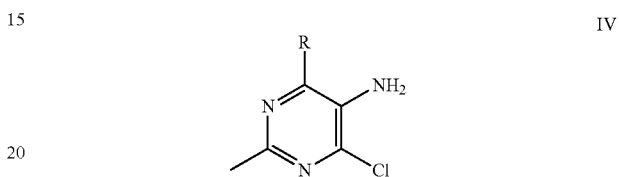

wherein R is one selected from the group consisting of:

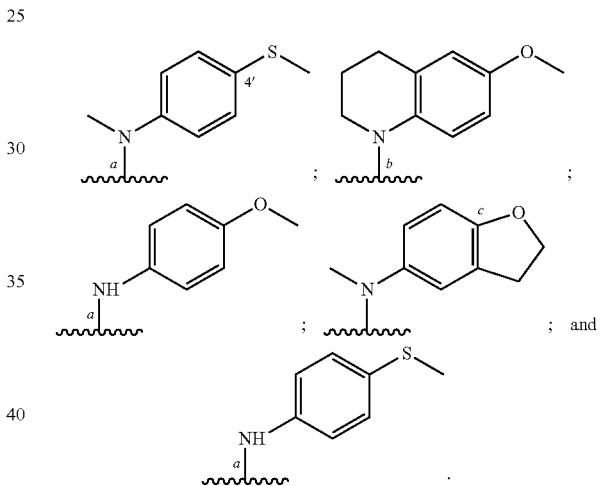

Another embodiment of this invention provides a compound of Formula V, and a salt thereof:

FORMULA V

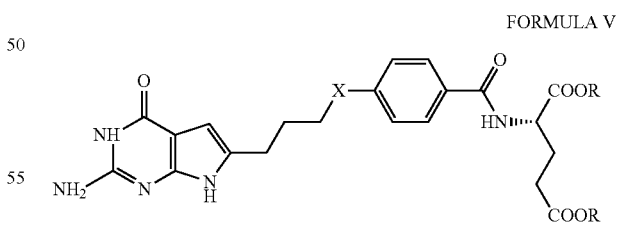

wherein X is selected from the group consisting of O, S, and NH, and wherein R is H or an alkyl group having from one to ten carbon atoms. Preferably, the compound of Formula V is wherein X is S and R is H.

Another embodiment of this invention provides a pharmaceutical composition comprising a compound of Formula V and a pharmaceutically acceptable salt thereof:

FORMULA V

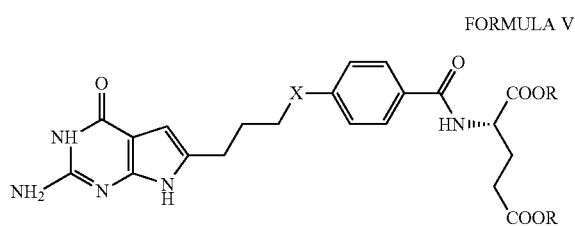

wherein X is selected from the group consisting of O, S, and NH, and wherein R is H or an alkyl group having from one to ten carbon atoms. Preferably, the pharmaceutical composition comprises a compound of Formula V wherein X is S and R is H.

Another embodiment of this invention provides a compound of Formula VI, and salts thereof:

VI

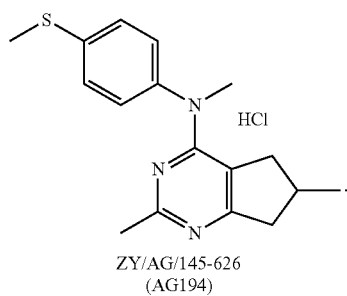

ZY/AG/145-626
(AG194)

Another embodiment of this invention provides a pharmaceutical composition comprising a compound of Formula VI and a pharmaceutically acceptable salt thereof:

VI

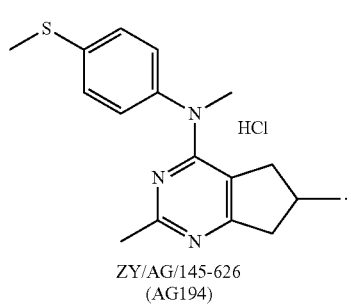

ZY/AG/145-626
(AG194)

Another embodiment provides a compound of Formula VII, and salts thereof:

VII

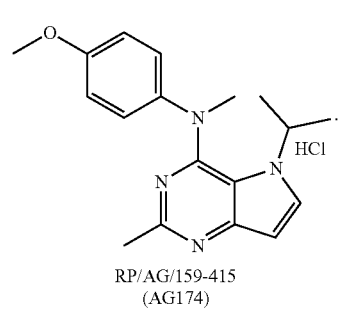

RP/AG/159-415
(AG174)

Another embodiment of this invention provides a pharmaceutical composition comprising a compound of Formula VI and a pharmaceutically acceptable salt thereof:

VII

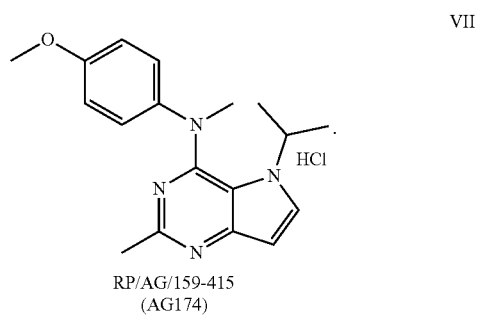 [SMILES: COc1ccc(N(C)c2nc(C)nc3ccn(C(C)C)c23)cc1 ; Cl]

RP/AG/159-415
(AG174)

In other embodiments of this invention, a method of treating a patient having cancer is provided comprising administering to a patient a therapeutically effective amount of a compound of Formula I, II, III, IV, V, VI, or VII, or administering to the patient a therapeutically effective amount of a pharmaceutical composition comprising a compound of either Formula I, II, III, IV, V, VI, or VII to the patient, for treating cancer. The cancer may be for example without limitation, leukemia, non-small cell lung cancer, colon cancer, central nervous system cancer, melanoma, ovarian cancer, cervical cancer, renal cancer, prostate cancer, breast cancer, and brain cancer.

Other embodiments of this invention provide for pharmaceutically acceptable salts of the compounds of this invention. The compounds of this invention may be made into acid salts that are water soluble. Most preferably, these water soluble salts of the compounds of this invention may be formulated into oral dosage forms providing orally administered active antitumor agents.

Section I:

The following provides preferred compounds of Formula I (1, 2, 3, 4, and 5 below) and the structural formula of a known chemotherapeutic agent combretastatin A-4:

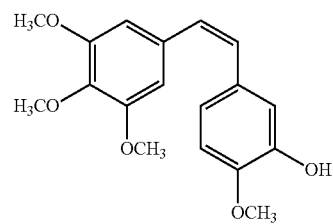

combretastatin A-4

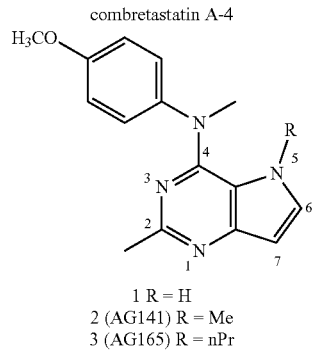

1 R = H
2 (AG141) R = Me
3 (AG165) R = nPr

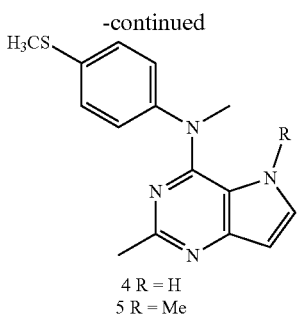

4 R = H
5 R = Me

The present applicant has previously disclosed that certain pyrrolo[3,2-d]pyrimidines exhibit excellent antitumor effects and RTK inhibitory activity.[7,8] In addition these agents have been reported to have activity in cell lines overexpressing P-glycoprotein and β-III tubulin, thus overcoming resistance pathways common to some antimicrotubule agents including paclitaxel.[9] Compounds 1.HCl (i.e. HCl salt of compound 1)-3.HCl (i.e. the HCl salt of compound 3) were evaluated for their activity against receptor tyrosine kinases (RTKs) overexpressed by tumor endothelial cells. It was discovered that the inhibitory potencies of these analogs were comparable with the clinically used drugs sunitinib and erlotinib against VEGFR2 (see Table 1). Compounds 1-3 also displayed excellent anti-proliferative effects in the MDA-MB-435 cancer cell line and microtubule depolymerization activities with $IC_{50}$s in nanomolar range, comparable to CA-4 (Table 2). Compounds 2 (AG141) and 3 (AG165) were designed to induce a conformational restriction on the 4-anilino moiety by introducing alkyl substituents on the 5-N of the pyrrole ring (compound 3 has a n-propyl (nPr) group at the 5-N position of the pyrrole ring, and compound 2 has a methyl (Me) group at the 5-N position of the pyrrole ring). Compounds 4 and 5 with 4'-SCH$_3$ substitution were synthesized as bioisosteric analogs of 1 and 2 respectively (see above structures). Also see Formula VII for the structure of AG174 (having a branched propyl (isopropyl)group at the 5-N position of the pyrrole ring).

TABLE 1

RTK and A431 inhibitory activities (IC$_{50}$ ± SD) of compounds 1-3.

|  | Kinase inhibition IC$_{50}$ [whole-cell assays] (nM) | | | A431 cytotoxicity (nM) |
|---|---|---|---|---|
|  | VEGFR2 | PDGFR-β | EGFR |  |
| 1 · HCl | 182.3 ± 20.6 | 250.2 ± 20.6 | 29.5 ± 3.1 | 215.2 ± 30.1 |
| 2 · HCl (AG141) | 30.5 ± 5.3 | 67.0 ± 10.2 | 25.2 ± 0.41 | 8.8 ± 0.9 |
| 3 · HCl (AG165) | 52.0 ± 6.7 | >200 | 89.3 ± 9.2 | 107.1 ± 18.0 |
| sunitinib | 18.9 ± 2.7 | 83.1 ± 10.1 | 172.1 ± 19.4 | ND |
| erlotinib | 124.7 ± 18.2 | 12.2 ± 1.9 | 1.2 ± 0.2 | ND |

ND—Not Determined
"HCl" = hydrochloride salt

TABLE 2

Antiproliferative effects and microtubule depolymerizing activities of compounds 1-3.

|  | MDA-MB-435 IC$_{50}$ (nM) | Microtubule depolymerization EC$_{50}$ (nM) |
|---|---|---|
| 1 · HCl | 96 ± 5.3 | 1200 |
| 2 · HCl (AG141) | 4.3 ± 0.3 | 7.4 |
| 3 · HCl (AG165) | 8.8 ± 3.4 | 20 |
| CA-4 | 3.47 ± 0.6 | 13.1 |

"HCl" = hydrochloride salt

Synthesis Scheme Chemistry of Compounds of Section I:

Acid catalyzed condensation of pyrrole 6 with acetonitrile led to the pyrrolo[3,2-d]pyrimidine 7 in 86% yield. Chlorination with POCl$_3$ generated 8 in 79% yield. Nucleophilic displacements of 8 using N-methyl-p-anisidine and (4-methylthio)-N-methyl-aniline afforded 1 and 4 respectively in 72% and 65% yields. Alkylation of the 5-N with appropriate alkyl halides resulted in 2, 3 and 5 in 89%, 76% and 80% yields respectively.

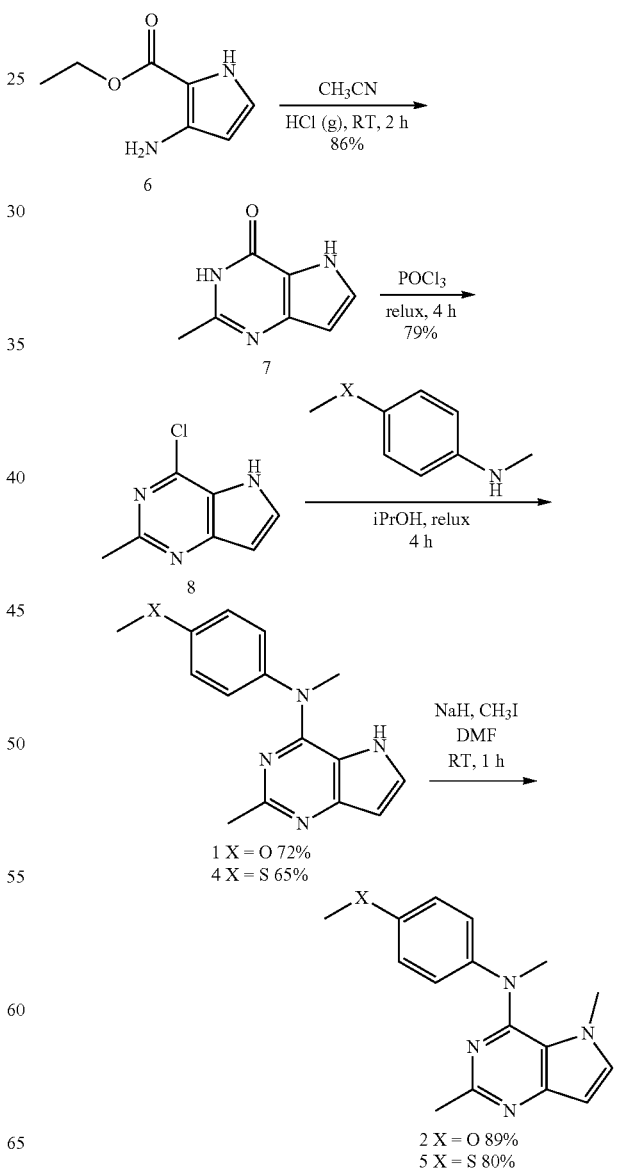

-continued

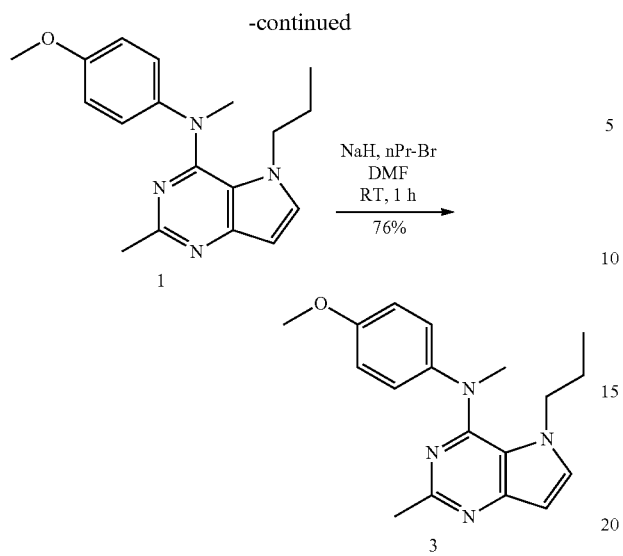

Biological Evaluation of Section I Compounds:
Table 3.
Table 3 shows antiproliferative effects and microtubule depolymerizing activities of compounds 4 and 5.

TABLE 3

|  | MDA-MB-435 IC$_{50}$ (nM) | Microtubule depolymerization EC$_{50}$ (nM) |
|---|---|---|
| 4 · HCl | 49.9 ± 10.4 | 1100 |
| 5 · HCl | 6.2 ± 1.0 | 23 |
| CA-4 | 3.47 ± 0.6 | 13.1 |

"HCl" = hydrochloride salt

Methylation of the pyrrole 5-N led to significant improvement in MDA-MB-435 IC$_{50}$ for both 4-methoxy (2 over 1, ~20 fold improvement) and 4'-thiomethyl analogs (5 over 4, ~7 fold improvement). This could be attributed in part, to the conformational restriction afforded by the methyl group. Clearly, in addition to the conformational restriction, other factors such a transport, metabolism, pharmacokinetics could also play a role in the increased potency of 5 over 4 and 2 over 1 respectively.

Figure 2:
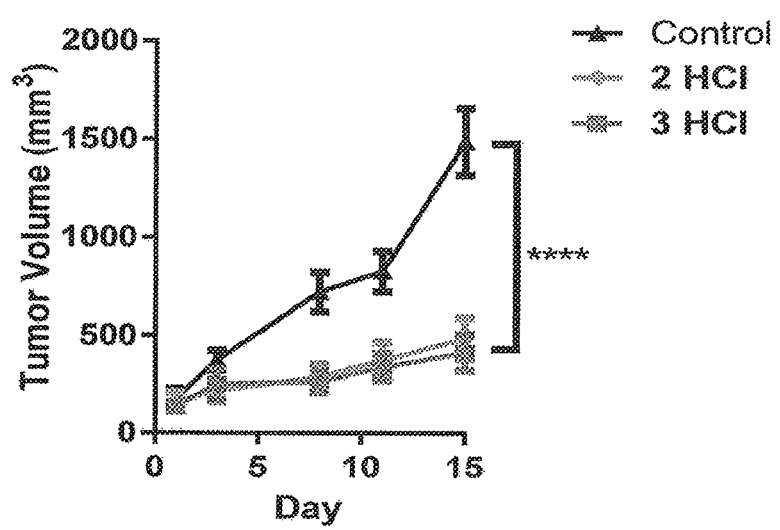
FIG. 2 shows tumor volumes during the trial on treatment with 2.HCl (AG141) and 3.HCl (AG165). Arrows indicate treatment days. n=7-10 tumors and data points represent mean±SEM.
Figure 3:
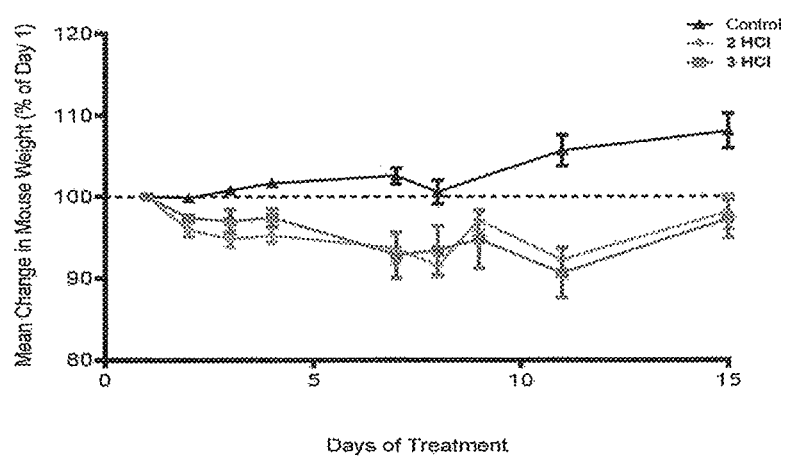
FIG. 3 shows the percent change in mouse weight during the trial on treatment with 2.HCl (AG141) and 3.HCl (AG165). n=7-10 tumors and data points represent mean±SEM.
Figure 4:
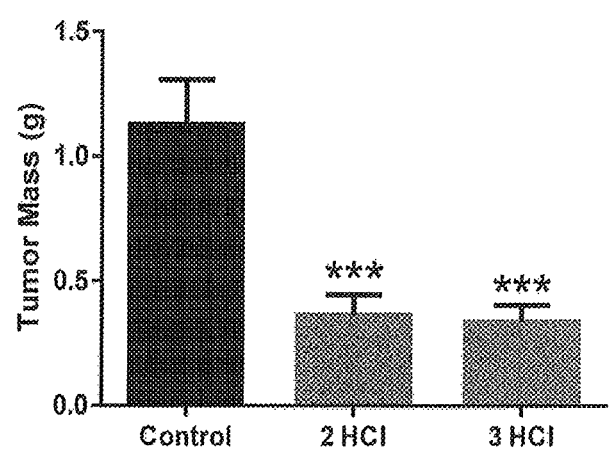
FIG. 4 shows the final average tumor mass on Day 15. n=7-10 tumors and data points represent mean±SEM. ***$p<0.001$.

MDA-MB-435 Xenograft Trial
  MDA-MB-435 cells were implanted subcutaneously into both flanks of nude mice.
  Mice were treated with MTD and schedule using IP injections of 75 mg/kg.
  Cumulative dose=525 mg/kg for 3.HCl (AG165) (dosed days 1, 2, 3, 4, 7, 9, and 11), and 375 mg/kg for 2.HCl (AG141) (dosed days 1, 2, 3, 4, and 9).
  Tumor volume was determined using tumor length, width, and height measured with calipers.
  Two-way repeated measures ANOVA with post hoc testing was used to analyze the datasets.
  FIG. 2 shows the tumor volumes during the trial on treatment with 2.HCl (AG141) and 3.HCl (AG165). Arrows indicate treatment days. n=7-10 tumors and data points represent mean±SEM.
  FIG. 3 shows the percent change in mouse weight during the trial on treatment with 2.HCl (AG141) and 3.HCl (AG165). n=7-10 tumors and data points represent mean±SEM.
  FIG. 4 shows the final average tumor mass on Day 15. n=7-10 tumors and data points represent mean±SEM. ***p<0.001

Both 2.HCl (AG141) and 3.HCl (AG165) inhibited tumor growth during the trial. They caused recoverable weight loss as compared to the vehicle. In addition both these compounds displayed statistically significant (p<0.001) lower final average tumor mass compared to the vehicle; however, 2.HCl (AG141) caused noticeable adverse effects on the central nervous system. In contrast 3.HCl (AG165) did not induce any noticeable adverse effects or toxicities while retaining antitumor efficacy. Therefore, this compound was chosen to evaluate against paclitaxel in the more aggressive MDA-MB-231 xenograft model.

Figure 5:
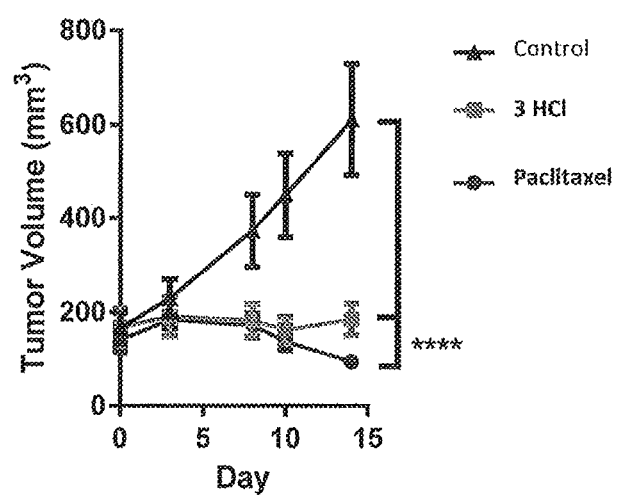
FIG. 5 shows the tumor volumes during the trial on treatment with 3.HCl (AG165), paclitaxel and control. The comparisons in tumor volume between control and drugs are indicated for the last day (****=$p<0.0001$). n=7-10 tumors and data points represent mean±SEM.

MDA-MB-231 Xenograft Trial
  3.HCl (AG165) displayed statistically significant antitumor effects (p<0.001) and showed no apparent toxicity. Hence, it was selected for further study in an aggressive tumor model.
  The cumulative dose of paclitaxel was 60 mg/kg with 10 mg/kg IP injections and cumulative dose of 3.HCl (AG165) was 450 mg/kg with 75 mg/kg IP injections (dosed days 1, 2, 3, 8, 9, 10 for each drug).
  FIG. 5 shows the tumor volumes during the trial on treatment with 3.HCl (AG165), paclitaxel and control. The comparisons in tumor volume between control and drugs are indicated for the last day (****=p<0.0001). n=7-10 tumors and data points represent mean±SEM.
  3.HCl (AG165) showed statistically significant antitumor effects comparable to paclitaxel in the MDA-MB-231 xenograft model. Thus, we have identified 3.HCl (AG165) as a water-soluble, dual acting RTK/tubulin inhibitory agent that addresses some critical limitations of existing therapies and demonstrates in vivo antitumor effects with an acceptable toxicity profile. Further studies are currently underway to extend the complete SAR of these pyrrolo[3,2-d]pyrimidines as multi-targeted agents and to evaluate these compounds in other tumor models as potential anticancer agents.

IC50 and EC50 Data of Section I Compounds:
Table 3a.
Table 3a below shows the IC50 and EC50 data for compounds of this invention. In Table 3a, for the compounds of this Section, the "R" group is the moiety set forth in the second vertical column of table 3a. This "R" group is identified as "R$_3$" in Formulae I and II, above, respectively.

TABLE 3a

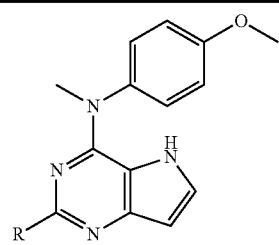

1-4

TABLE 3a-continued

[Structure 5-8: tetrahydroquinoline-methoxy with pyrrolopyrimidine, R group, NH]

5-8

[Structure 9-12: N-methyl-N-(4-methylthiophenyl) pyrrolopyrimidine, R group, NH]

9-12

[Structure 13-16: N-methyl-N-(methoxynaphthyl) pyrrolopyrimidine, N-Me, R]

13-16

| | | IC50 ± SD in MDA-435 Cells | EC50 for Microtubule Depolymerization in A · 10 Cells |
|---|---|---|---|
| 1 | H AG86 (RP) | 193 ± 39 nM | 5.7 μM |
| 2 | Me AG85 (RP) | 96.6 ± 5.3 nM | 1.2 μM |
| 3 | Cl AG336 (KS) | 18.3 ± 5.0 | 309 nM |
| 5 | H AG331 (KS) | ND | — |
| 6 | Me AG 142 (RP) | 21.0 ± 3.6 nM | 39.2 nM |
| 7 | Cl AG335 (KS) | 9.2 ± 1.8 | 78 |
| 9 | H AG351 (KS) | ND | >10 micro |
| 10 | Me AG313 (KS) | 49.9 ± 10.4 nM | 1.1 μM |
| 11 | Cl AG347 (KS) | 17.2 ± 3.4 | 576 nM |
| 13 | H AG362 (KS) | ND | ND |
| 14 | Me AG333 (KS) | 2000 | >10000 |
| 15 | Cl AG421 (KS) | 22.6 | 50 |

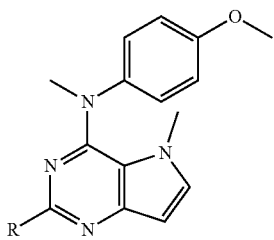

17-20

TABLE 3a-continued

[Structure 21-24: tetrahydroquinoline-methoxy with N-methyl pyrrolopyrimidine, R]

21-24

[Structure 25-28: N-methyl-N-(4-methylthiophenyl) N-methyl pyrrolopyrimidine, R]

25-28

[Structure 29: N-methyl-N-(4-OCF3-phenyl) N-methyl pyrrolopyrimidine, 2-Cl]

29

| | | IC50 ± SD in MDA-435 Cells | EC50 for Microtubule Depolymerization in A · 10 Cells |
|---|---|---|---|
| 17 | H AG380 (KS) | 13.4 ± 0.5 | 27.5 |
| 18 | Me AG141 (RP) | 4.3 ± 0.3 | 7.4 |
| 19 | Cl AG381 (KS) | 1.3 ± 0.0 | 1.48 |
| 21 | H AG379 (KS) | 30.5 ± 0.8 | 75 |
| 22 | Me AG142 (RP) | 21.0 ± 3.6 | 39.2 |
| 23 | Cl AG4I3 (KS) | 4.1 ± 0.1 | 3.31 |
| 25 | H KS-404 | | |
| 26 | Me AG312 (KS) | 6.2 ± 1.0 nM | 23 nM |
| 27 | Cl AG412 (KS) | 3.6 ± 0.3 | 2.7 |
| 29 | AG401 (KS) | 49.3 ± 1.1 | 138.7 |

Table 3b set forth below sets forth EGFR kinase inhition, Flk-1 kinase inhibition, A431 cyctotoxicity, U251 cytotoxicity, and CAM (gi50) data for the indicated compounds off this invention.

TABLE 3B

| 2- | 5- | | EGFR kinase inhibition | Flk-1 kinase inhibition | PDGFR kinase inhibition | A431 cytotoxicity | U251 cytotoxicity | CAM (gi50) |
|---|---|---|---|---|---|---|---|---|
| 3 Cl | 5-NH | AG336 | 91.5 ± 5.1 | 241.5 ± 51.2 | 204.4 ± 9.8 | 30.5 ± 1.7 | 80.9 ± 14.7 | 322 ± 88.2 |
| 7 Cl | 5-NH | AG335 | 478.3 ± 67.3 | 1040.0 ± 200.1 | 1420.4 ± 207.4 | 239.3 ± 40.1 | 39.8 ± 5.9 | 520.7 ± 92.3 |
| 18 Me | 5-NMe | AG141 | 89.3 ± 9.2 | 52.0 ± 6.7 | >200 | 107.1 ± 18.0 | | |
| 19 Cl | 5-NMe | AG381 | 6.3 ± 0.9 | 12.4 ± 1.2 | 4.2 ± 0.9 | 2.1 ± 0.3 | 3.1 ± 0.4 | 9.3 ± 0.91 |
| 23 Cl | 5-NMe | AG413 | 9.0 ± 0.9 | 15.2 ± 2.0 | 8.4 ± 0.8 | 3 ± 0.3 | 3.8 ± 0.5 | 7.6 ± 1.0 |
| 26 Me | 5-NMe | AG312 | 54.8 ± 9.2 | 543.6 ± 77.2 | 450.2 ± 53.1 | 18.8 ± 4.1 | 35.1 ± 6.3 | 362.6 ± 56.9 |
| 27 Cl | 5-NMe | AG412 | 16.4 ± 2.6 | 33.9 ± 3.9 | 10.8 ± 1.6 | 8.2 ± 1.3 | 11.3 ± 1.8 | 45.2 ± 5.2 |

Section II:

This Section II of this application describes the design, synthesis, biological evaluation of Cyclopenta[d]pyrimidines as antitubulin agents and the discovery of N-(4-Methylthiophenyl) and N-(4-Dimethylaminophenyl) Substituted N,2-dimethyl-cyclopenta[d]pyrimidines as long acting and potent microtubule targeting agents.

Figure 6:
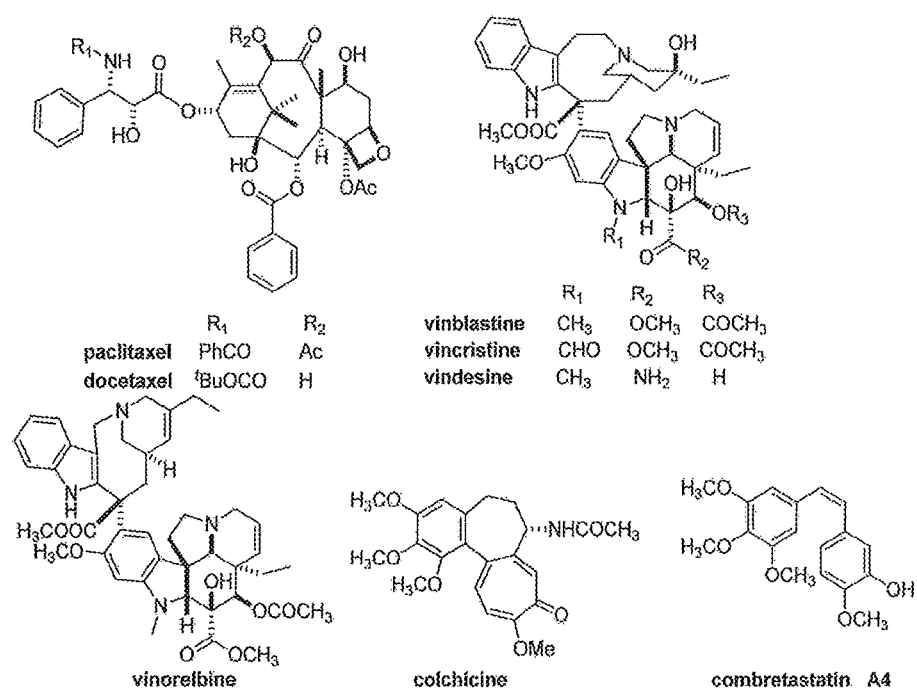
FIG. 6 shows the structures of known microtubule targeting agents.

Known tubulin binding agents (FIG. 6), widely used in cancer chemotherapy, belong to an important class of antitumor agents. Three well established classes of tubulin binding agents are classified on the basis of their interactions within the taxoid, vinca and colchicine sites on tubulin. Taxoid binding agents stabilize microtubules, while vinca and colchicine site agents inhibit microtubule formation and cause loss of cellular microtubules. Drugs, including paclitaxel (Taxol), cabazitaxel (Jevtana) and docetaxel (Taxotere) and the epothilones and several other chemotypes bind to β-tubulin at a site on the interior of the microtubule within the taxoid site. Taxoids are useful in the treatment of breast, lung, ovarian, head and neck and prostate cancers. The vinca domain microtubule disrupting agents bind to β-tubulin at the αβ interface between different tubulin dimers. Among them, vincristine, vinblastine, vinorelbine and eribulin are successful anticancer agents. A diverse collection of small molecules along with colchicine and the combretastatins bind to the colchicine site on β-tubulin at its interface with α-tubulin within a single tubulin dimer.[1]

The expression of P-glycoproteins (Pgp), a drug efflux pump, and βIII-tubulin, one of many β-tubulin isotypes, are clinically established microtubule drug resistance mechanisms. Colchicine site agents are reported that are non-Pgp substrates and possess the ability to circumvent βIII tubulin mediated drug resistance. Although colchicine itself is not used as an antitumor agent, there are numerous colchicine site agents that have been evaluated in clinical trials, including 2-methoxyestradiol, combretastatin A-4 (CA-4), the phosphorylated prodrug combretastatin A-4 phosphate (CA-4P, fosbretabulin), the combretastain A-1P prodrug (OXi4503), BNC105P, ABT-751 and plinabulin (NPT-2358). However, to date no colchicine site agent has advanced to Phase III studies, attesting to the necessity to develop viable colchicine site agents for potential cancer chemotherapy.[2]

Section II Compounds Rationale:

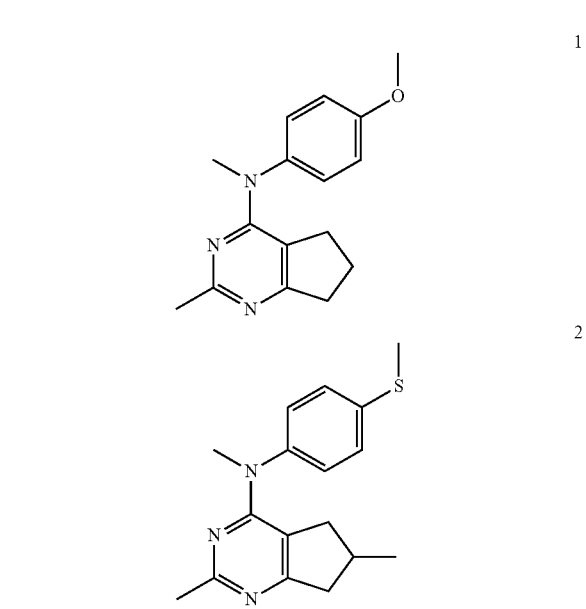

Structures of the Lead Compounds 1 and 2 and their Antiproliferative Activities.

We have disclosed compounds 1 and 2 (above) as potent antiproliferative agents. In the previous structure-activity relationship (SAR) studies of cyclopenta[d]pyrimidine based-antitubulin agents, we demonstrated the importance of the para-methoxyphenyl moiety for biological activities. Literature[4-6] suggests that the major metabolism of the methoxyphenyl moiety was likely an O-demethylation. In order to increase the potency and in vivo stability of 1, modifications, in this study, were focused on the variation of the para-methoxy anilino moiety of 1. Compound 3 (Table 4), the para-methylthiophenyl substituted cyclopenta[d]pyrimidne, was designed to decrease the possible demethylation. An in vitro metabolism study showed that the principal metabolite of the methylsulfide in 3, with human liver microsomes, was the methylsulfinyl group, and one of the minor metabolites was the methyl sulfonyl group. Thus, the methylsulfinyl analog 4 (Table 4) and the methylsulfonyl analog 5 (Table 4) were also synthesized to determine their antiproliferative potencies. Compounds 6 and 7 (Table 4) were designed to restrain the conformation of the para-methoxyl group, which could also prevent the proposed metabolism pathway of compound 1 due to steric and/or electronic effects. The electron donating, para-methylamino moiety of 8 (Table 1) and the para-dimethylamino moiety of 9 (Table 4) were designed as isosteric replacements of the O-methoxy moiety. According to the literature,[7] 8 should be the major metabolite of 9. Compounds 10-12 (Table 4), with a 4-methoxyphenylmethyl, were devised to exploit the relative large binding space in the 4-methoxyphenyl binding pocket of the colchicine site, as suggested by a previous docking study.[3] The next structural modifications involved the phenyl group. Compound 13 (Table 4), replaced the phenyl ring with a cyclohexyl ring to determine the importance of π-stacking interaction of the aniline ring. The variations proposed of compounds 10-13 would also serve as structural means to decrease the O-demethylation. Compound 3 and its major metabolite 4 are potent antitumor agents, which suggests that 3 could be a potential long acting agent. Similarly, 9 could also function as a potential long acting agent, since the metabolites of both 3 and 9 are anticipated to be potent compounds against tumor cells.

Section II Compounds Chemistry:

Scheme 1. Synthesis of intermediate compound 16.

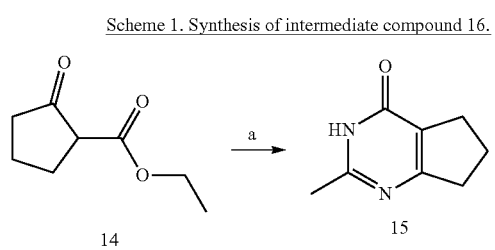

Reagents and conditions: (a) Acetamidine hydrochloride, Kt-OBu, DMF, 120° C., 79%; (b) POCl₃, 100° C., 4 h, 73%.

Scheme 2. Synthesis of aniline derivatives and related intermediates.

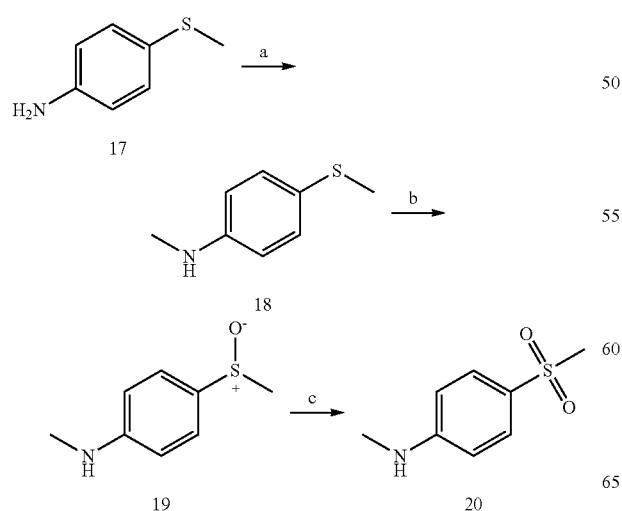

-continued

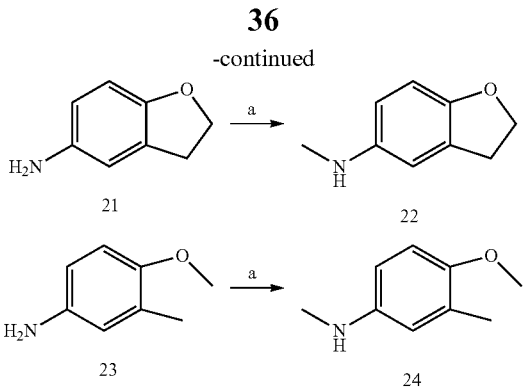

Reagents and conditions:
(a) NaH, THF, CH₃I, 0° C., 65-75%;
(b) mCPBA (1.1 eq.), ACN, 0° C., 1 h, 67%;
(c) mCPBA (1.1 eq.), ACN, 0° C., 1 h, 59%.

Scheme 3. Synthesis of aniline derivatives and related intermediates.

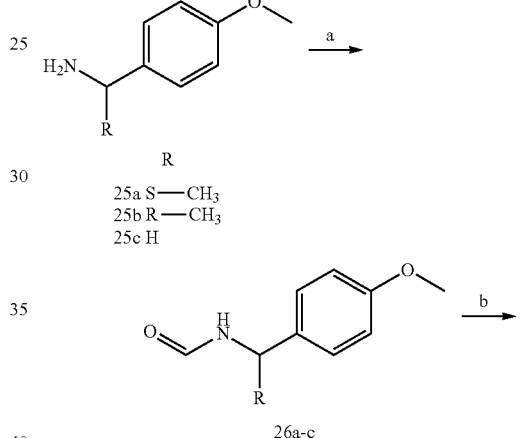

-continued

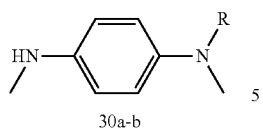
30a-b

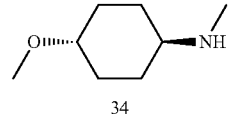
34

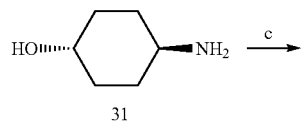
31

Reagents and conditions:
(a) HCOOH, Ac₂O, DCM, r.t., 4-6 h;
(b) THF, LAH, 60° C., 53-72%;
(c) CBzCl, ACN, TEA, 0° C., 90%;
(d) NaH, THF, CH₃I, 0° C., 68%;
(e) MeOH, Pd/C, H₂ (55 psi), 2 h, 92%.

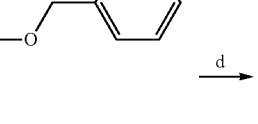
32

Scheme 4. General synthesis of target compounds 3-13.

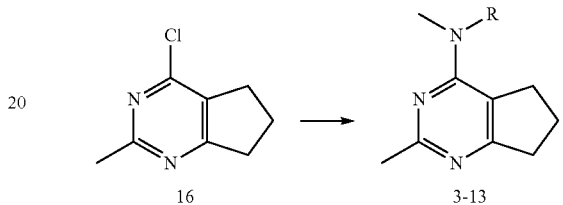
16 → 3-13

Reagents and conditions: compounds 18-20, 22, 24, 27a-c, 30a-b, 34, dioxane, HCl (2N in doxane, 1 drop), µW, 120-160° C., 3-6 h, 61-93%.

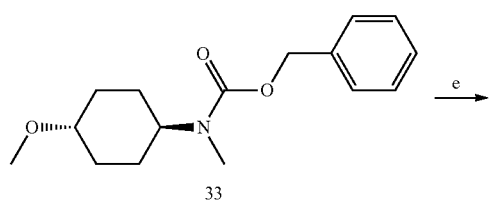
33

Biological Evaluation and SAR of Section II Compounds

TABLE 4

$IC_{50}$ values for inhibition of proliferation of MDA-MB-435 cells and $EC_{50}$ values for disruptive effect on microtubule polymerization in A-10 cells.

| Compd | structure | $IC_{50} \pm SD$ (MDA-MB-435) Cancer cells (nM) | $EC_{50}$ in A-10 cells (Concentration that causes 50% tubulin loss in A-10 cells) (nM) |
|---|---|---|---|
| 1 | 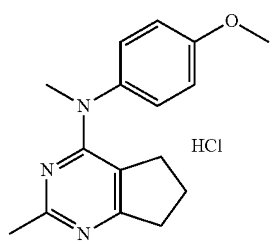 | 7.0 ± 0.7 | 25.9 |
| 2 | 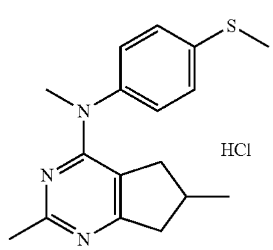 | 15.0 ± 6.5 | 116 |
| 3 | 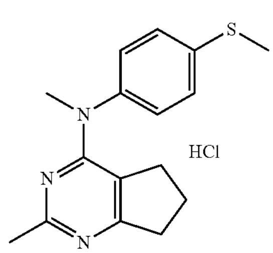 | 4.6 ± 0.5 | 12.6 |

TABLE 4-continued

IC$_{50}$ values for inhibition of proliferation of MDA-MB-435 cells and EC$_{50}$ values for disruptive effect on microtubule polymerization in A-10 cells.

| Compd | structure | IC$_{50}$ ± SD (MDA-MB-435) Cancer cells (nM) | EC$_{50}$ in A-10 cells (Concentration that causes 50% tubulin loss in A-10 cells) (nM) |
|---|---|---|---|
| 4 | 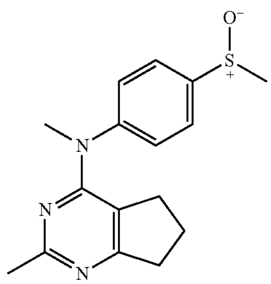 | 7.9 ± 0.49 | 31 |
| 5 | 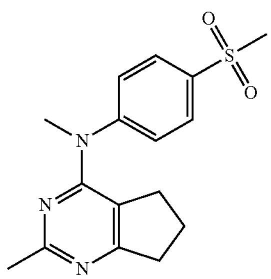 | ND | >10 000 |
| 6 | 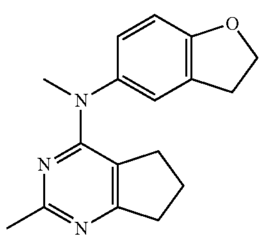 [SMILES: Cc1nc2c(c(N(C)c3ccc4c(c3)CCO4)n1)CCC2] | 12.1 ± 0.9 | 70 |
| 7 | 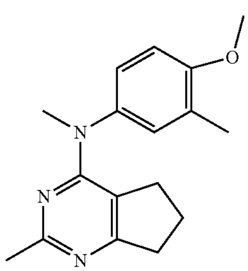 | 18.4 ± 1.9 | 56 |
| 8 | 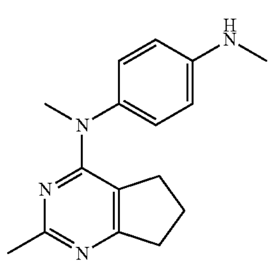 | 20 ± 1.9 | 45 |

TABLE 4-continued

IC$_{50}$ values for inhibition of proliferation of MDA-MB-435 cells and EC$_{50}$ values for disruptive effect on microtubule polymerization in A-10 cells.

| Compd | structure | IC$_{50}$ ± SD (MDA-MB-435) Cancer cells (nM) | EC$_{50}$ in A-10 cells (Concentration that causes 50% tubulin loss in A-10 cells) (nM) |
|---|---|---|---|
| 9 | 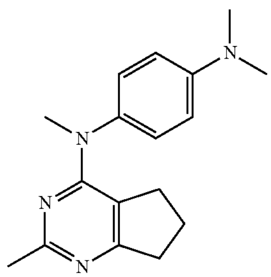 | 8.2 ± 0.62 | 40 |
| 10 | 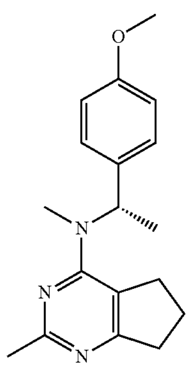 [SMILES: COc1ccc([C@H](C)N(C)c2nc(C)nc3c2CCC3)cc1] | ND | >10 000 |
| 11 | 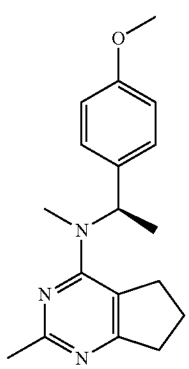 [SMILES: COc1ccc([C@@H](C)N(C)c2nc(C)nc3c2CCC3)cc1] | ND | >10 000 |
| 12 | 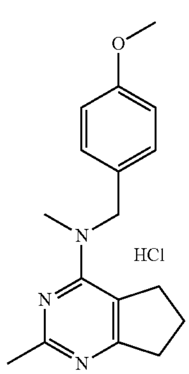 [SMILES: COc1ccc(CN(C)c2nc(C)nc3c2CCC3)cc1 ; Cl] | 450.0 ± 13.5 | 11 300 |

TABLE 4-continued

IC$_{50}$ values for inhibition of proliferation of MDA-MB-435 cells and EC$_{50}$ values for disruptive effect on microtubule polymerization in A-10 cells.

| Compd | structure | IC$_{50}$ ± SD (MDA-MB-435) Cancer cells (nM) | EC$_{50}$ in A-10 cells (Concentration that causes 50% tubulin loss in A-10 cells) (nM) |
|---|---|---|---|
| 13 | 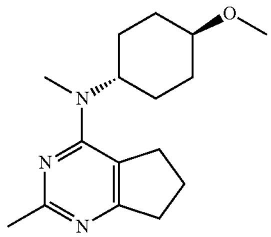 | ND | >10 000 |
| CA-4 | | 3.4 ± 0.6 | 13.0 |

Compounds 3-13 were tested for their antiproliferative effects against the drug sensitive MDA-MB-435 cancer cells in culture using a sulforhodamine B (SRB) assay with the antitubulin agents CA-4 and compound 1 as positive controls. The microtubule disrupting effects of these compounds were observed in a cell-based phenotypic assay. See also AG194, structure set forth as Formula VI, herein.

TABLE 5

Inhibition of tubulin assembly and colchicine binding by CA-4 and 3-9.

| | Inhibition of tubulin | Inhibition of colchicine binding % Inhibition ± SD | |
|---|---|---|---|
| Compd. | assembly IC$_{50}$ (µM) ± SD | 5 µM inhibitor | 1 µM inhibitor |
| 1 | 1.6 ± 0.1 | 92 ± 0.7 | 70 ± 2 |
| 2 | 1.9 ± 0.1 | 60 ± 2 | 84 ± 3 |
| 3 | 1.3 ± 0.1 | 92 ± 3 | 74 ± 5 |
| 4 | 1.1 ± 0.06 | 93 ± 3 | 79 ± 4 |
| 6 | 1.1 ± 0.007 | 83 ± 4 | 59 ± 5 |
| 7 | 1.2 ± 0.09 | 85 ± 4 | 64 ± 5 |
| 9 | 1.2 ± 0.01 | 85 ± 3 | 65 ± 4 |
| CA-4 | 1.3 ± 0.1 | 98 ± 0.6 | 87 ± 0.2 |

The effects of 3, 4, 6, 7 and 9 on the polymerization of purified tubulin were evaluated (Table 5). This allows a study of the direct interaction of these compounds with their intracellular target. The ability of these compounds to bind to the colchicine site on tubulin was evaluated by measuring inhibition of [$^3$H]colchicine binding to tubulin.

TABLE 6

Compound activity in parental and Pgp expressing cell line

| | IC$_{50}$ ± SD (nM) | | |
|---|---|---|---|
| Compd. | Parental SK-OV-3 | Pgp expressing SK-OV-3 MDR1-6-6 | Rr* |
| 1 | 11.3 ± 0.2 | 16.4 ± 0.4 | 1.5 |
| 2 | 21.2 ± 4.0 | 22.7 ± 2.7 | 1.1 |
| 3 | 7.2 ± 0.6 | 9.28 ± 0.42 | 1.3 |
| 4 | 12.6 ± 0.3 | 18 ± 4 | 1.4 |
| 6 | 18.7 ± 1.2 | 29.8 ± 5.6 | 1.6 |
| 7 | 23.9 ± 2.5 | 47.5 ± 2.4 | 2.0 |
| 8 | 36.3 ± 3.3 | 49.7 ± 7.9 | 1.4 |
| 9 | 13.0 ± 1.0 | 22.6 ± 2.3 | 1.7 |
| CA-4 | 4.5 ± 0.2 | 6.6 ± 1.3 | 1.5 |
| Paclitaxel | 3.0 ± 0.06 | 2600 ± 270 | 864 |

The ability to circumvent Pgp-mediated drug resistance was evaluated using an SK-OV-3 isogenic cell line pair (Table 6).

TABLE 7

Effects of compounds in parental and overexpressing β-III cells.

| | IC$_{50}$ ± SD (nM) | | |
|---|---|---|---|
| Compd. | Parental HeLa | β-III overexpressing HeLa | Rr* |
| 1 | 12.0 ± 1.2 | 9.6 ± 0.9 | 0.8 |
| 2 | 19.6 ± 2.0 | 14.8 ± 1.5 | 0.8 |
| 3 | 6.95 ± 0.53 | 5.26 ± 0.78 | 0.8 |
| 4 | 6.83 ± 0.35 | 10 ± 1 | 1.5 |
| 6 | 16.0 ± 1.0 | 15 ± 1 | 0.9 |
| 7 | 23.0 ± 1.0 | 18.8 ± 1.6 | 0.8 |
| 8 | 31.0 ± 1.6 | 19.1 ± 3.9 | 0.6 |
| 9 | 11.0 ± 1.0 | 9.8 ± 0.9 | 0.9 |
| CA-4 | 4.7 ± 0.2 | 5.7 ± 0.4 | 1.2 |
| Paclitaxel | 1.6 ± 0.2 | 7.7 ± 0.2 | 4.7 |

Another clinically relevant drug resistance mechanism of tubulin-targeting agents is the overexpression of the βIII isotype of tubulin. The ability of compounds 3, 4 and 6-9 to overcome βIII tubulin mediated drug resistance was examined using an isogenic HeLa cell line pair (Table 7).

Metabolite Identification Study of 3

TABLE 8

Summary of 3 metabolites identified by LC/MS/MS.

| Metabolite | RT (min) | Metabolite (m/z) | Met ID | MS Peak Area in 60 min sample HPLC area | Percentage (%) |
|---|---|---|---|---|---|
| 3 | 17.4 | 286 | Parent | 2,061,000 | 46.4 |
| M1 (5) | 7.9 | 318 | Sulfone | 98,900 | 2.2 |
| M2 (4) | 9.6 | 302 | Sulfoxide | 2,199,500 | 49.5 |
| M3 | 9.9 | 318 | Di-hydroxy | 57,156 | 1.3 |
| M4 | 15.5 | 302 | Hydroxy | 81,795 | 1.8 |
| M5 | 16.0 | 302 | Hydroxy | 92,546 | 2.1 |

FIG. 7 shows the Identification the metabolites of section II compound 3 by LC/MS/MS. FIG. 7a) HPLC spectra of 3 incubated with human liver microsomes at 0 and 60 min. Metabolites M1-M5 and parent 3 were illustrated on the spectra. FIG. 7b) MS and MS/MS spectrum of 3. FIG. 7c) MS and MS/MS spectrum of M1 (compound 5). FIG. 7d)

Figure 7A:
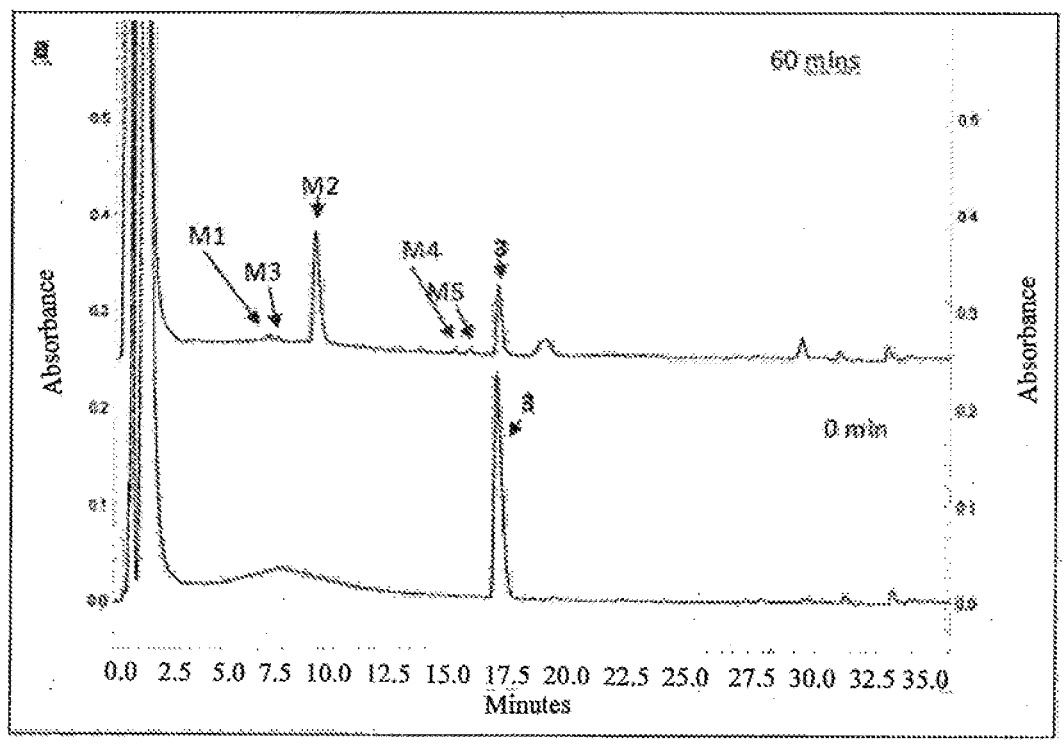
FIGS. 7A, 7B, 7C, 7D and 7E show the Identification the metabolites of section II compound 3 by LC/MS/MS.
Figure 7B:
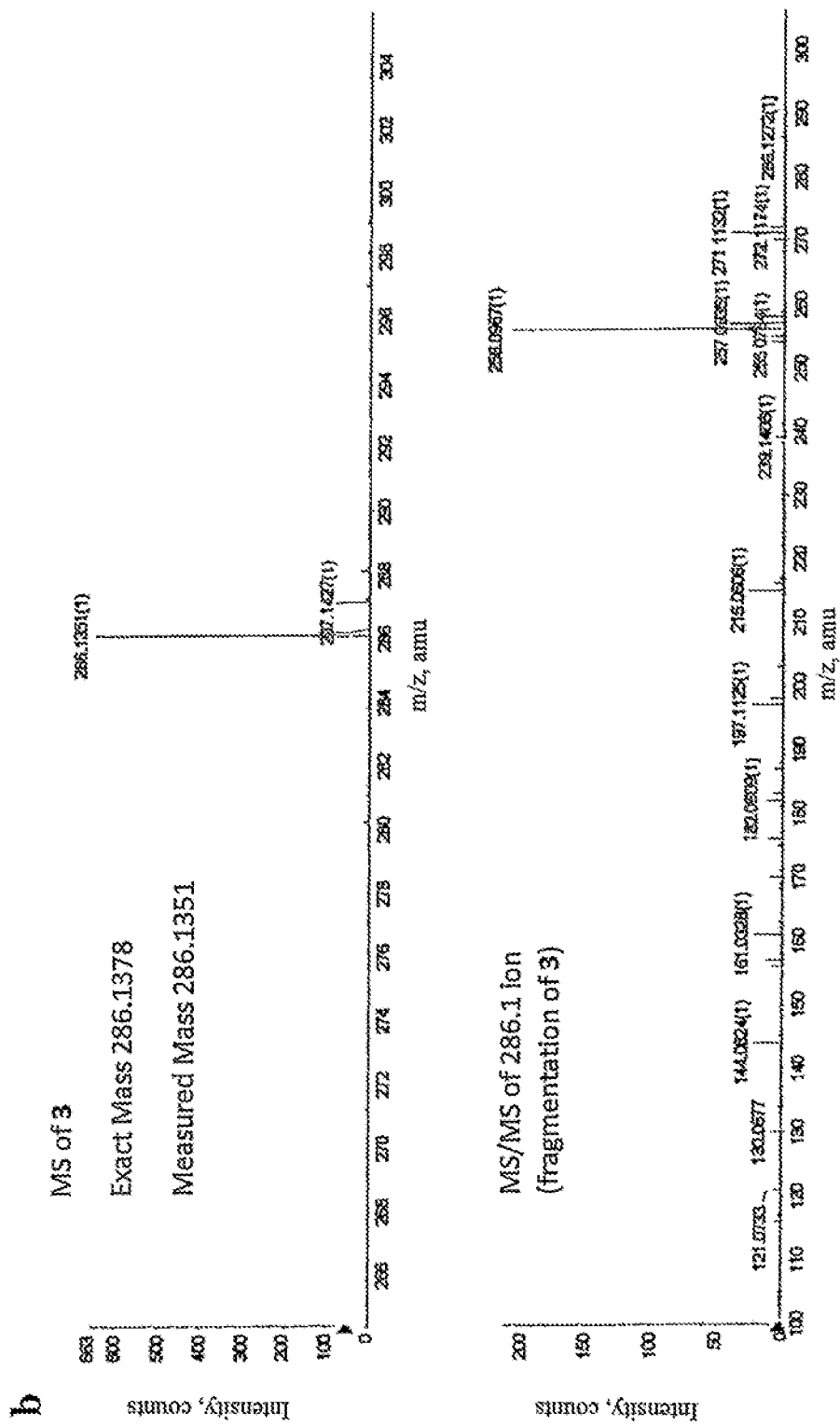
Figure 7C:
Figure 7D:
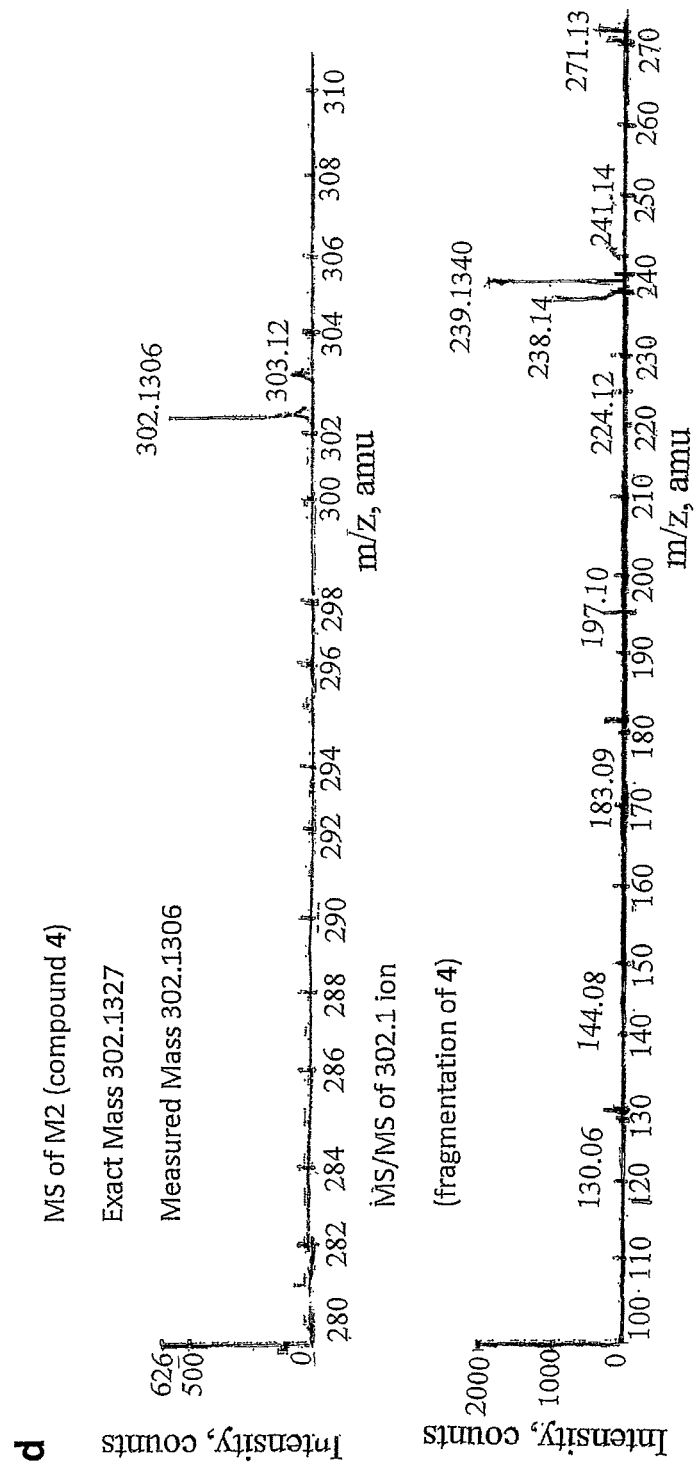
Figure 7E:
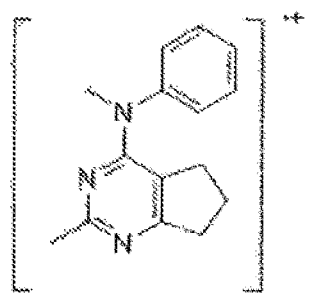

MS and MS/MS spectrum of M2 (compound 4). FIG. 7e) Fragmentation of M1 and M2 (MS/MS 239.1340).

Figure 8:
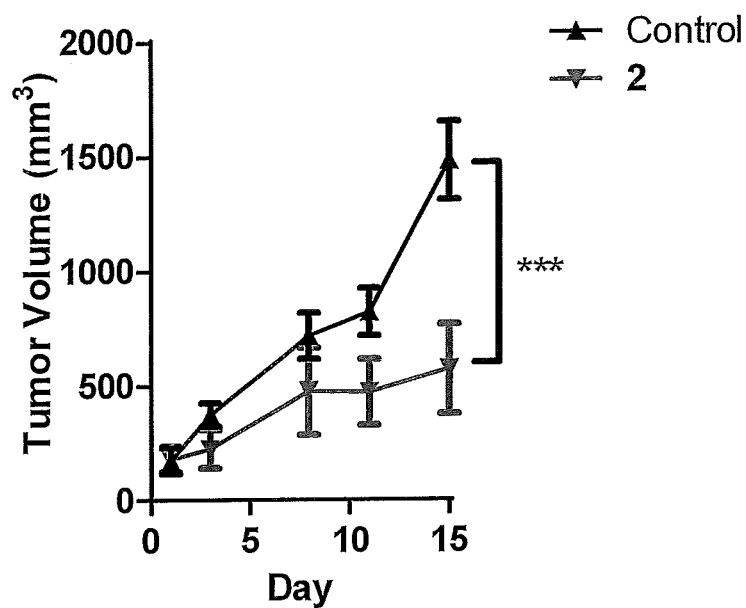
FIG. 8 shows the in vivo evaluation of compound 2, Section II, and the utility of this analog as an antitumor agent.

FIG. 8 shows in vivo evaluation of 2 (i.e compound 2 HCl, Section II) and the utility of this analog as an antitumor agent.

Section III:
Substituted Monocyclic Pyrimidines as Potent Tubulin Inhibitors that Circumvent P-Glycoprotein Mediated Resistance Microtubules play a crucial role in the development and maintenance of cell shape, cell division and alterations of cell signaling and trafficking. In a recent report[1], it was revealed that microtubule targeting agents (MTAs) inhibit a majority of human tumors by interfering with essential interphase functions such as microtubule trafficking. Many distinct classes of MTAs have been identified (FIG. 6) with two classes playing major roles in current cancer treatment. The taxanes, such as paclitaxel and docetaxel, (FIG. 6) are utilized for the treatment of breast, lung, ovarian, and prostate carcinomas.[2] The vinca alkaloids, including vincristine, vinblastine, and vinorelbine, (FIG. 6) are most often used for treatment of leukemias, lymphomas, and non-small cell lung cancer. MTAs can be classified into two groups on the basis of their mechanisms of action: (i) microtubule-stabilizing agents or polymerizing agents (exemplified by taxanes) and (ii) microtubule destabilizing agents (exemplified by vincas).[3] Taxane site agents bind to the interior of the microtubule on β-subunits. In contrast, the vinca site agents bind to the vinca site on tubulin, which is formed at the interface between α- and β-subunits of different tubulin heterodimers on an aberrant polymer morphologically distinct from microtubules. Another drug-binding site on tubulin—the colchicine site—inhibits tubulin polymerization.[4] The colchicine site is primarily on β-tubulin at its interface with the α-subunit of the same tubulin heterodimer. Colchicine site binding agents, as exemplified by combretastatin A-4 (CA-4), (FIG. 6) are currently in clinical trials for cancer treatment. CA-4P, the phosphorylated prodrug of CA-4, is currently being evaluated in multiple tumor types, which demonstrates the significance of developing colchicine site agents for potential use as MTAs and antitumor agents.[5]

Multidrug resistance (MDR) is a major limitation of clinically used anticancer agents, and MDR tumors are usually resistant to microtubule disrupting agents. Overexpression of P-glycoprotein (Pgp) has been reported in the clinical setting in several tumor types, particularly after patients have received chemotherapy.[6] Moreover, Pgp expression may act as a prognostic indicator in certain cancers and is associated with poor response to chemotherapy by fostering resistance in the presence of cytotoxic drug.[7]

Section III Compounds: Target Compounds 2-6

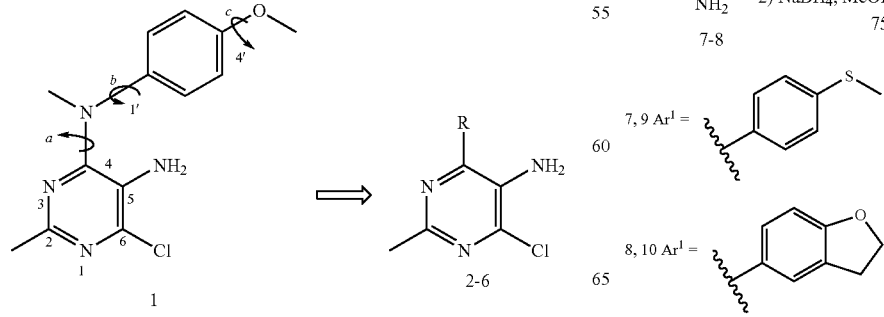

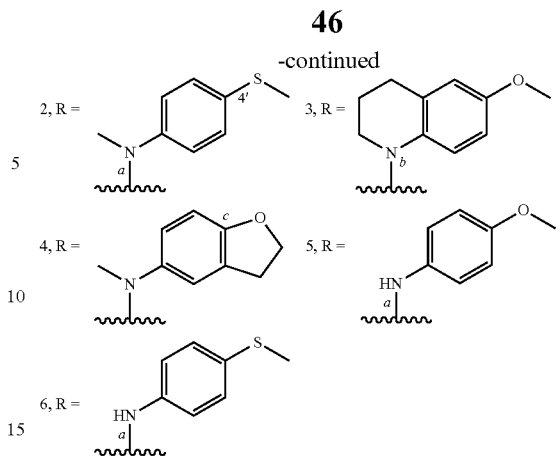

Figure 9:
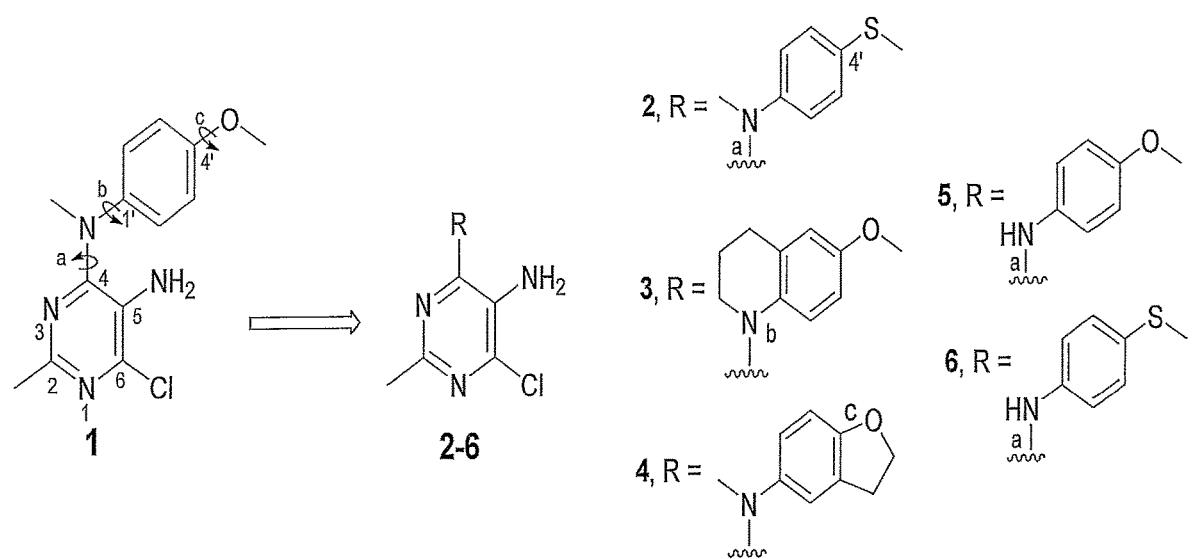
FIG. 9 shows the structures of the monocyclic pyrimidine compounds of this invention.

Recently, Gangjee et al.[8] reported a potent monocyclic pyrimidine (1) with the N-methyl-4'-methoxyaniline moiety at the 4-position (FIG. 9). This tubulin depolymerizing agent circumvented resistance issues that occur with antitubulin drugs, such as paclitaxel, while retaining its inhibition of cancer cells. This finding prompted a Structure-Activity Relationship (SAR study), and this report addresses the effect of bioisosterism, conformational restriction and flexibility on biological activity by introducing various anilines in the 4-position of the pyrimidine ring of 1. Bond rotations about 2 rotatable single bonds, b and c in the lead molecule 1 were restricted in new target compounds 3 and 4, respectively. New target compounds 5 and 6 were designed to evaluate the importance of the 4-NCH$_3$ and to increase the free rotation about the 4-position C—N bond (bond a) as well as the 1'-position C—N bond (bond b) in 1 and 2, respectively. New analog compounds 2-6 were synthesized and evaluated for their biological activity against tubulin assembly as well as against a cell line overexpressing the multidrug resistance protein Pgp. Tumors with Pgp impart significant resistance to many antitubulin agents, including paclitaxel, vincristine and vinblastine.

Section III Compounds' Chemistry:

Compounds 2-6 were synthesized as described in Scheme 1.

Scheme 1

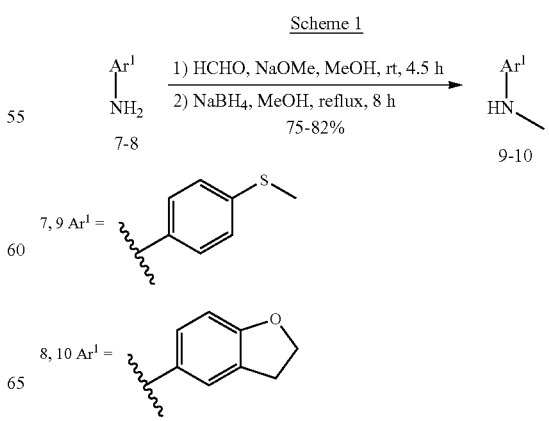

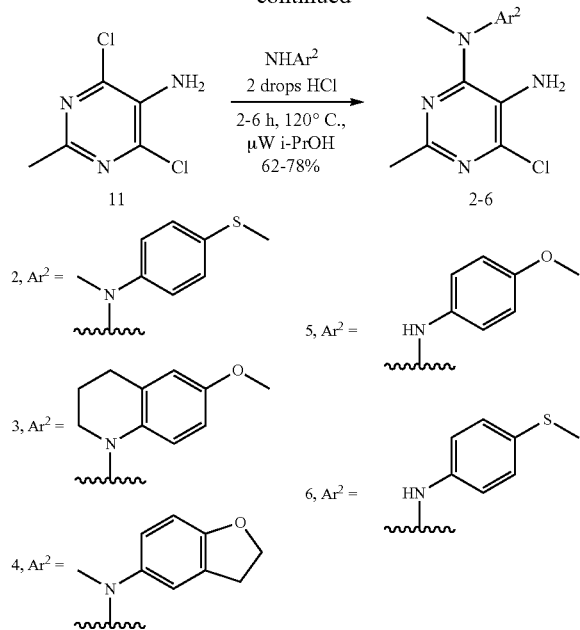

Anilines 7 and 8 were methylated using sodium methoxide and formaldehyde suspension in methanol and stirred for 4.5 h. Sodium borohydride was then added, and the solution kept at reflux for 2 h to afford compounds 9 and 10 in 75-82% yield. Dichloropyrimidine 11 (Scheme 1) was subjected to nucleophilic displacement with various anilines and a catalytic amount of concentrated HCl in the presence of i-PrOH to yield final compounds 2-6.

Biological Activity of Section III Compounds:

Compounds 2-6 of Section III were evaluated for inhibition of the polymerization of purified bovine brain tubulin. These compounds were compared with standard CA4 and lead 1 as inhibitors of tubulin assembly in a quantitative study (Table 9). Bioisosteric replacement of the 4'-methoxy of the lead 1 with a 4'-thiomethyl moiety gave (2) that retained potency against tubulin assembly. Compound 3, an analog with a conformationally restricted 6'-methoxy-tetrahydroquninoline moiety was found to be 2.5-fold less active than the standard CA4. A fused bicyclic 4-N-methyl-2'-3'-dihydrobenzofuran moiety at the 4-position (4) was tolerated, albeit with a 4-fold reduction in potency as an inhibitor of tubulin polymerization. Conformationally flexible 5 with a N—H at the 4-position of the pyrimidine ring was inactive. The removal of the methyl moiety on the N4 of analog 2 led to a compound (6) with a 6-fold loss in activity against tubulin assembly. This study reveals that bioisoteric replacement of the 4'-methoxy group of the 4-aniline with a 4'-thiomethyl has a minor effect on activity. Restriction of the free rotation about the single bonds b and c in 1 by introducing conformational restriction led to a 1.5-4-fold loss in activity against tubulin inhibition. The removal of the 4-NCH$_3$ of 1 and 2 is detrimental for antitubulin activity. The ability of the potent compounds to inhibit binding of radiolabeled colchicine to tubulin were also measured to determine the binding site of compounds 1-6. At a 5 µM concentration, compounds 2 and 3 inhibited [$^3$H]colchicine binding by 51-65% in comparison to CA4 and 1 at 97% and 81% inhibition, respectively. These results suggest additional binding sites for 2 and 3 on tubulin.

TABLE 9

Inhibition of Tubulin Assembly and Inhibition of Colchicine Binding

| Section III Compd | Inhibition of tubulin assembly IC$_{50}$ ± SD (µM) | Inhibition of colchicine binding (% inhibition ± SD) 5 µM |
|---|---|---|
| CA4 | 1.2 ± 0.1 | 97 ± 0.02 |
| 1 | 2.1 ± 0.04 | 81 ± 0.3 |
| 2 | 2.6 ± 0.03 | 65 ± 0.4 |
| 3 | 3.0 ± 0.2 | 51 ± 4 |
| 4 | 8.8 ± 0.5 | — |
| 5 | >20 (partial activity) | — |
| 6 | 16 ± 0.5 | — |

The ability of 2-4 to circumvent Pgp-mediated drug resistance was evaluated using an OVCAR-8 isogenic cell line pair (Table 10). In this cell line pair, the Rr (relative resistance) of paclitaxel is 500 while Rr values of less than 1 were obtained with 2-4, consistent with the Rr values obtained with CA4 of 1.5. Remarkably, compounds 2-4 are 1.8-5-fold more potent in the Pgp overexpressing cell line as compared with the parental line, indicating a possible utility against resistant ovarian (and other) cancers due to Pgp overexpression. Mechanistic studies are currently underway to determine the reason(s) for this unusual finding. These data suggest that 2-4 are poor substrates for transport by Pgp and thus have advantages over other clinically used tubulin-targeting drugs like paclitaxel. Thus 2-4 inhibit the proliferation of human cancer cells without regard to the Pgp expression status.

TABLE 10

Compounds 1-4, Section III, Circumvent Pgp Mediated Resistance

| | Effect of Pgp on drug sensitivity$^a$ IC$_{50}$ ± SD (nM) | | |
|---|---|---|---|
| Compd | Parental OVCAR-8 | P-gp Overexpressing NCI/ADR-RES | Rr$^b$ |
| paclitaxel | 10.0 ± 0 | 5,000 ± 0 | 500 |
| CA4 | 6 ± 0.7 | 9.0 ± 2 | 1.5 |
| 1 | 25 ± 5 | 20 ± 0 | 0.8 |
| 2 | 310 ± 100 | 170 ± 7 | 0.55 |
| 3 | 500 ± 100 | 210 ± 10 | 0.42 |
| 4 | 3100 ± 900 | 630 ± 40 | 0.2 |

$^a$Antiproliferative effects of 1-4 in parental and MDR-1 cell lines in comparison with other microtubule disrupting agents. The IC$_{50}$ values were determined using the SRB assay (n = 3 (SD).
$^b$Rr: Relative resistance. The Rr was calculated by dividing the IC$_{50}$ of the Pgp overexpressing cell line by the IC$_{50}$ of the parental cell line. The OVCAR-8 and NCI/ADR-RES cell lines were generously provided by the NCI.

Compounds of Section III Discussion:

Compounds 2-6, Part III, were designed, synthesized and evaluated as tubulin inhibitors and as antitumor agents. Restricting the rotation about the 1'-position C—N bond (bond b) and the 4'-position C—O bond (bond c) led to a 1.5-4-fold decrease in activity against tubulin compared to the lead compound 1. Biososteric replacement of the 4'-OCH$_3$ with the 4'-SCH$_3$ was tolerable. The 4-NCH$_3$ moiety in compounds 1 and 2 is necessary for potent activity against tubulin, however, there could be other sites of binding on tubulin for these analogs. Compounds 2-3 inhibited [$^3$H]colchicine binding by 51-65%, indicating that these compounds probably bind to the colchicine site on tubulin. In addition, compounds 2-4 displayed better potency in a Pgp overexpressing tumor cell line as compared with its isogenic control, indicating that these analogs could be highly useful in Pgp overexpressing tumors.

Figure 10:
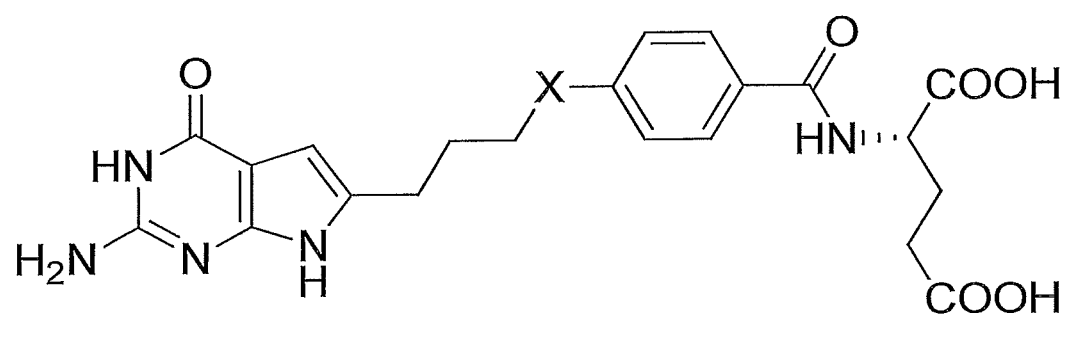
FIG. 10 shows the structures of three novel 6-substituted pyrrolo[2,3-d]pyrimidine compounds of this invention.
Figure 11A:
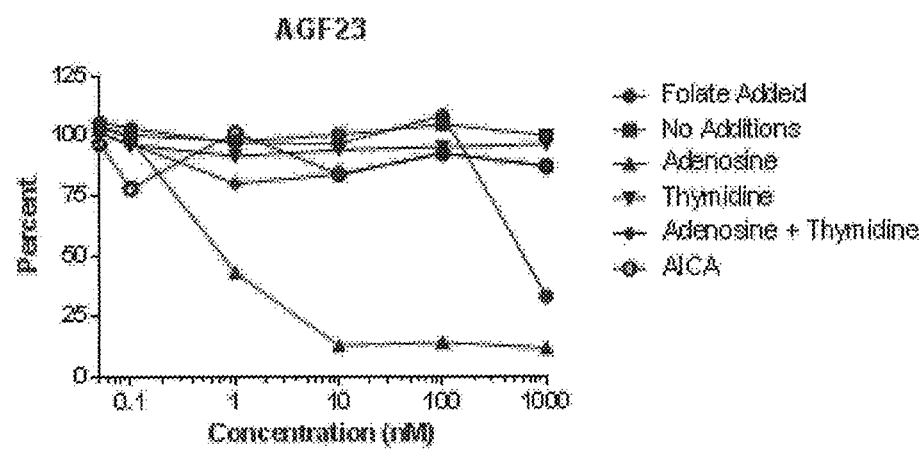
FIGS. 11A, 11B, 11C and 11D show the growth inhibition of KB cells by three novel 6-substituted pyrrolo[2,3-d] pyrimidine compounds of this invention, namely, AGF215, AGF234, and AGF263.
Figure 11B:
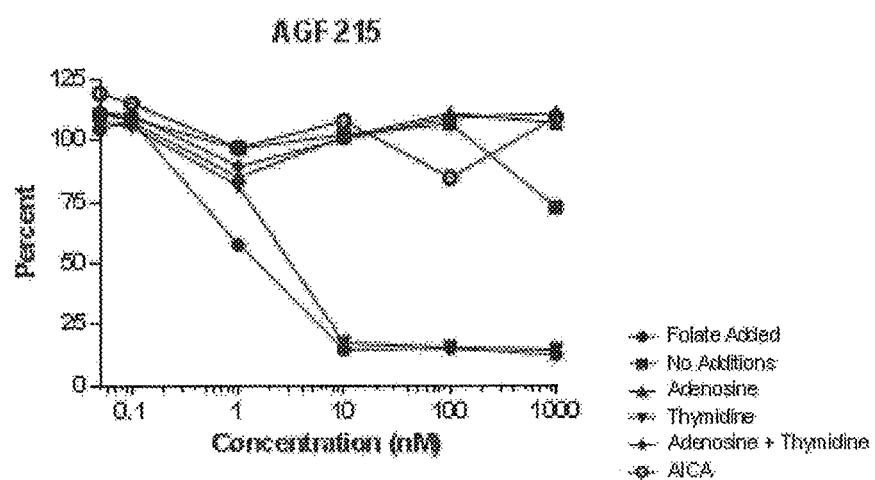
Figure 11C:
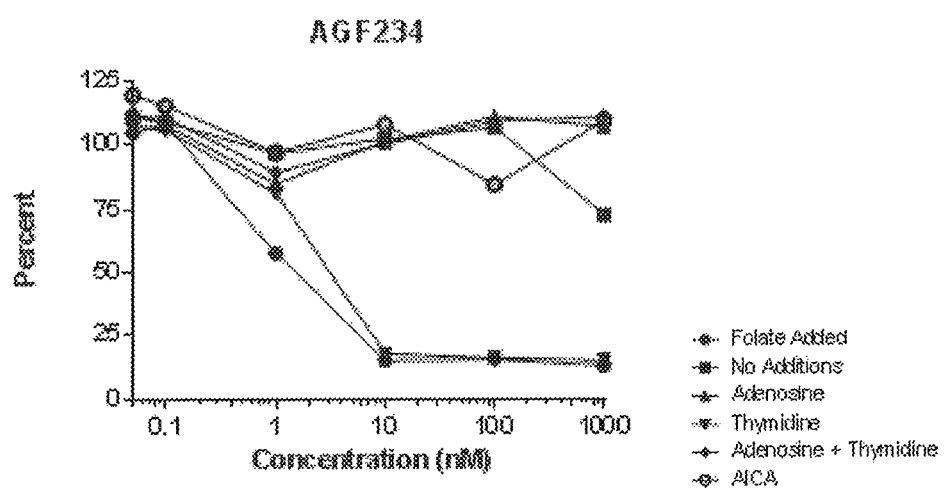
Figure 11D:
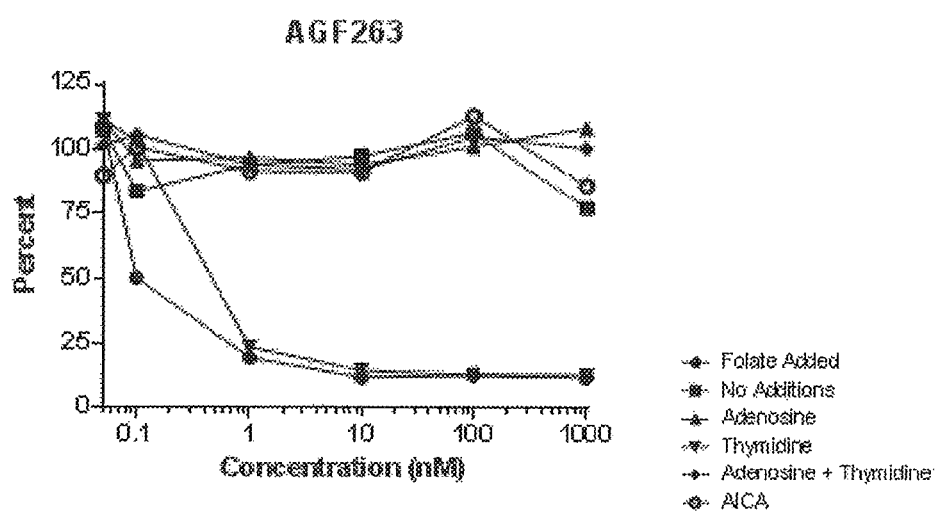

Section IV:
Synthesis and Biological Evaluation of Novel 6-Substituted Pyrrolo[2,3-d]pyrimidines as Targeted Antifolates Reduced folates are essential cofactors for the biosynthesis of purines and pyrimidines. Since humans do not synthesize folates, it is necessary to obtain these cofactors from dietary sources. In mammals, three specialized systems exist that mediate membrane transport of folates and antifolates across biological membranes.[13] These include the reduced folate carrier (RFC), the primary route for the uptake of folates and antifolates in mammalian cells, folate receptors (FRs) α and β, and the proton-coupled folate transporter (PCFT). Whereas RFC is ubiquitously expressed, FRs and PCFT show a narrower pattern of tissue expression.[2-4] Toxicity of clinically used antifolates is attributed in part to their lack of selectivity for tumor cells over normal cells mainly due to RFC transport. Antifolates with tumor-specific FR and/or PCFT drug uptake would decrease or eliminate major toxicities of currently used antifolates. We previously described the synthesis and biological activities of AGF23, a 6-substituted pyrrolo[2,3-d]pyrimidine. Against FRα- and PCFT-expressing KB human tumor cells, AGF23 was potently inhibitory ($IC_{50}$=1.9 nM).[8] Three novel isosteres of AGF23, namely AGF215, AGF234 and AGF263, with oxygen, nitrogen and sulfur in place of carbon at C11, respectively, were designed and synthesized, and are set forth as novel structures in Section IV of this application (see FIG. 10). This isosteric replacement of carbon with heteroatoms in the bridge affords compounds with different chain lengths, angles, conformations and extra hydrogen bond donors and/or acceptors compared to the parent carbon chain analog and were implemented to explore heteroatoms in the bridge region of AGF23 for biological activities.

The structures of the novel compounds AGF215, AGF234, and AGF263 are set forth as follows:

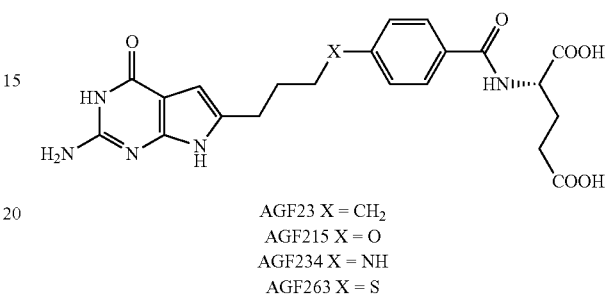

AGF23 X = $CH_2$
AGF215 X = O
AGF234 X = NH
AGF263 X = S

Synthesis Schemes of Section IV Compounds:

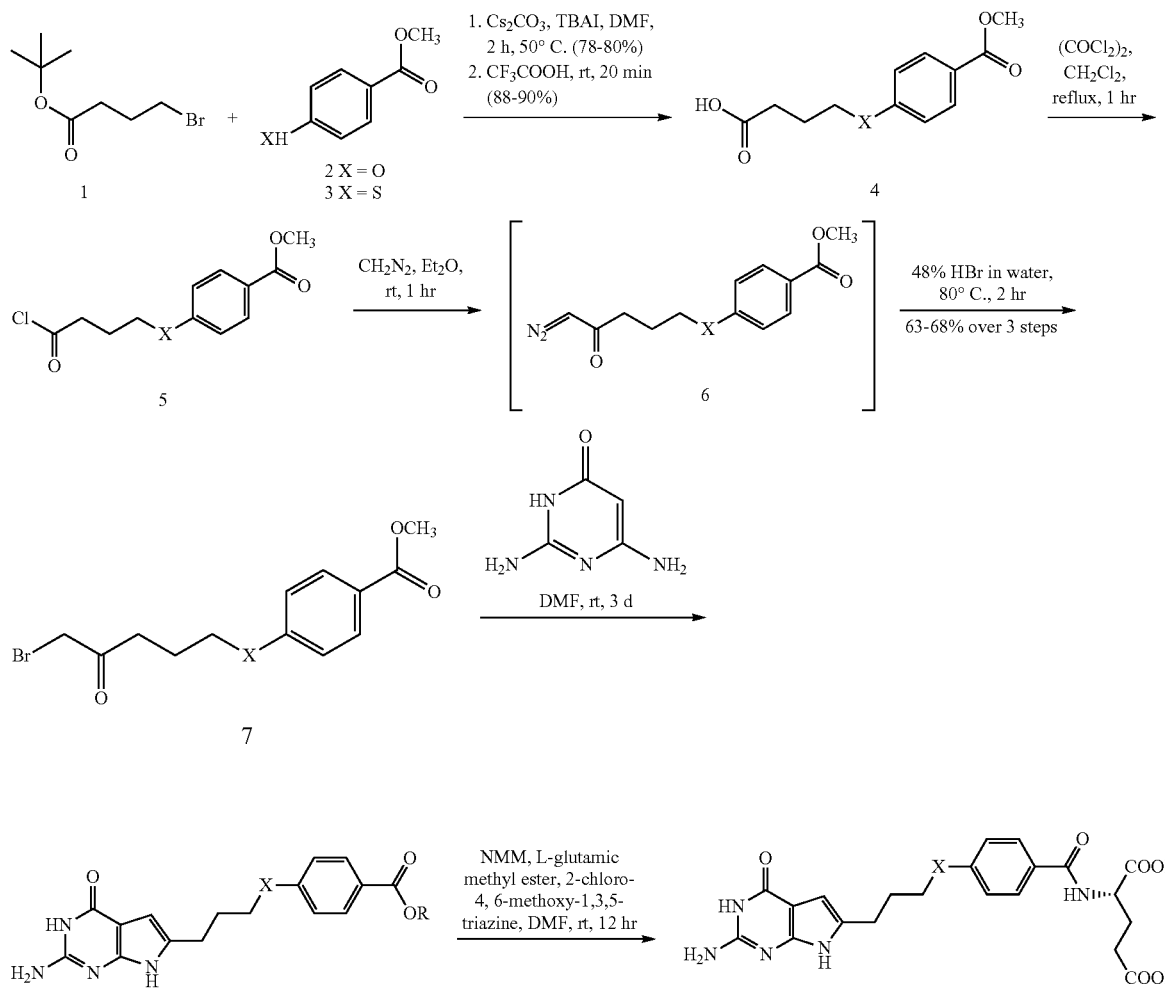

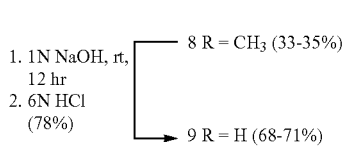 

Scheme 1:

A mixture of compounds 1 and 2 (compound 3 for sulfur) was treated with cesium carbonate and tetrabutylammonium iodide (TBAI) in DMF at 50° C. for 2 h. Ethyl acetate was added to the reaction mixture and the organic layer was washed with water and 2% HCl solution. The solvent was evaporated and the semisolid compounds obtained were dried overnight. The semisolid compounds were then treated with trifluoroacetic acid for 20 min. Excess trifluoroacetic acid was evaporated and the compounds 4 were purified using column chromatography. The carboxylic acids 4 were then converted to the acid chlorides and immediately reacted with diazomethane followed by 48% HBr in water to give the desired α-bromomethylketones 7. Condensation of 2,6-diamino-3H-pyrimidin-4-one with 7 at room temperature for 3 days afforded the 2-amino-4-oxo-6-substituted-pyrrolo[2,3-d]pyrimidines 8. Hydrolysis of 8 afforded the corresponding free acids 9. Subsequent coupling with L-glutamate dimethyl ester using 2-chloro-4,6-dimethoxy-1,3,5-triazine as the activating agent afforded the diesters 10. Final saponification of the diester gave the desired compounds AGF215 and AGF263.

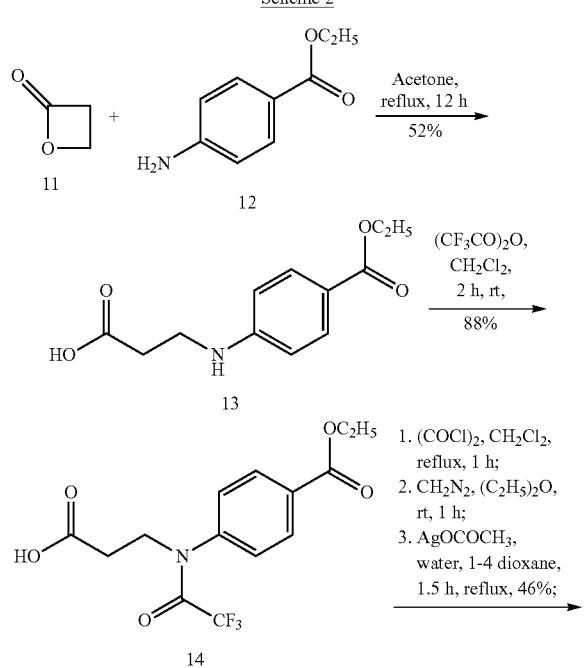

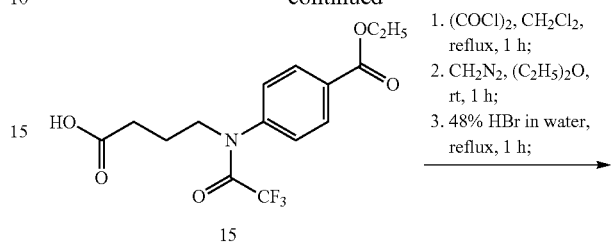

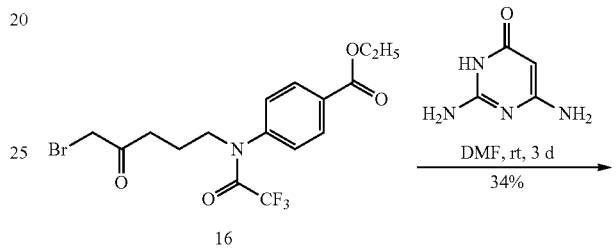

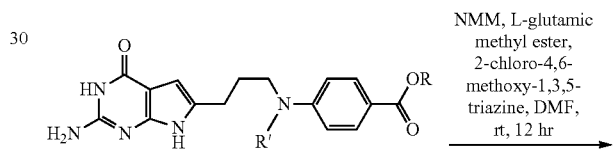

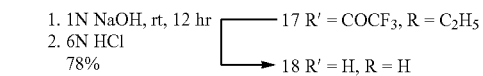

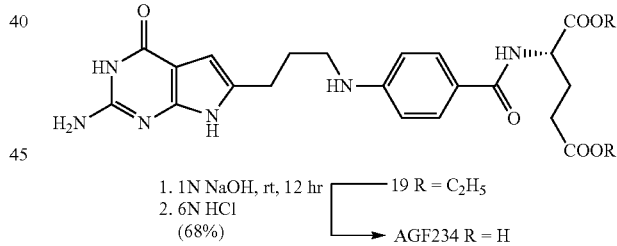

Scheme 2:

Carboxylic acid 13 was obtained from commercially available compound 11 and 3 using NaOH at 50° C. for 30 min. The carboxylic acid 13 was then converted to the acid chloride and immediately reacted with diazomethane, followed by silver acetate in water and dioxane at reflux for 1.5 h to give the desired carboxylic acid 15. Compound 15 was again converted to the acid chloride and immediately reacted with diazomethane followed by 48% HBr in water to give the desired o-bromomethylketone 16. Condensation of 2,6-diamino-3H-pyrimidin-4-one with 16 at room temperature for 3 days afforded 2-amino-4-oxo-6-substituted-pyrrolo[2,3-d]pyrimidine 17. Hydrolysis of 17 afforded the corresponding free acid 18. Subsequent coupling with the L-glutamate dimethyl ester using 2-chloro-4,6-dimethoxy-1,3,5-triazine as the activating agent afforded the diester 19. Final saponification of the diester gave the desired compound AGF234.

Biological Activity of Section IV Compounds

TABLE 11

IC$_{50}$s (in nM) for 6-substituted pyrrrolo[2,3-d]pyrimidine thienoyl antifolates AGF23, AGF215, AGF234, AGF263, and classical antifolates in RFC-, PCFT-, and FR-expressing cell lines.

| | RFC | | FRα | | FRβ | | PCFT | | RFC/FRα/PCFT | |
|---|---|---|---|---|---|---|---|---|---|---|
| Antifolate | PC43-10 | R2 | RT16 | RT16 (+FA) | D4 | D4 (+FA) | R2/hPCFT4 | R2 (VC) | KB | KB (+FA) |
| AGF23 | >1000 | >1000 | 6.3 (1.6) | >1000 | 5.6 (1.2) | >1000 | 213 (28) | >1000 | 1.9 (0.7) | >1000 |
| AGF215 | >1000 | >1000 | 3.47 (0.96) | >1000 | 3.80 (1.51) | >1000 | >1000 | >1000 | 1.54 (0.74) | 767 (117) |
| AGF234 | 670 (150) | >1000 | 1.4 (0.32) | 136 (34) | 0.84 (0.10) | 316 (26) | 268 (65) | 696 (158) | 0.74 (0.30) | 938 (17) |
| AGF263 | >1000 | >1000 | ND | ND | ND | ND | 592 | >1000 | 0.22 (0.05) | 600 (251) |
| MTX | 12 (1.1) | 114 (31) | 114 (31) | 216 (8.7) | 106 (11) | 211 (43) | 121 (17) | >1000 | 6.0 (0.6) | 20 (2.4) |
| PMX | 138 (13) | 42 (9) | 42 (9) | 894 (93) | 60 (8) | 254 (78) | 13.2 (2.4) | 974 (18) | 68 (12) | 327 (103) |
| RTX | 6.3 (1.3) | 15 (5) | 15 (5) | >1000 | 22 (10) | 746 (138) | 99.5 (11.4) | >1000 | 5.9 (2.2) | 22 (5) |
| LMTX | 12 (2.3) | 12 (8) | 12 (8) | >1000 | 2.6 (1.0) | 275 (101) | 38.0 (5.3) | >1000 | 1.2 (0.6) | 31 (7) |
| GW1843U89 | 11 (3.3) | 277 (81) | 277 (81) | >1000 | 52 (12) | >1000 | >1000 | >1000 | 5.8 (3.5) | 32 (15) |
| PT523 | 1.28 (0.18) | 409 (51) | 409 (51) | >1000 | ND | ND | >1000 | >1000 | 5.26 (1.07) | 2.90 (0.16) |

FIG. 11 shows the growth inhibition of KB cells by AGF23, and compounds of this invention AGF215, AGF234, and AGF263, and protection by excess folic acid, nucleosides, or 5-aminoimidazole-4-carboxamide (AICA). KB cells were plated (4000 cells/well) in folate-free RPMI 1640 medium with 10% dialyzed serum, antibiotics, L-glutamine, and 2 nM leucovorin with a range of concentrations of AGF23, AGF 154, AGF 152, or AGF 163 in presence of folic acid (200 nM), adenosine (60 µM) and/or thymidine (10 µM), or in the presence of AICA (320 µM). Cell proliferation was assayed with CellTiter-Blue™ with a fluorescent plate reader.

Molecular Modeling of Section IV Compounds:

Molecular Operating Environment (MOE), 2014.09 was used for docking and conformational analysis. Compounds AGF23, AFG215, AGF234 and AGF263 were docked in FRα bound to folic acid[9]. The 2-NH$_2$, 3-NH of AGF23, AFG215, AGF234 and AGF263 interact with the same amino acids as the corresponding groups of folic acid. The α-carboxylic acid of AFG215, AGF234 and AGF263 is oriented towards the γ-carboxylic acid of folic acid and forms a hydrogen bond with the Trp102 side chain. The γ-carboxylic acid of AGF23 is oriented towards the α-carboxylic acid of folic acid and forms a hydrogen bond with the Gly137 back bone. The docking scores of all four analogs were in the range of −9 to ~8.5 kcal/mol compared with folic acid of ~9.12 kcal/mol.

Since AGF23 was shown to target glycinamide ribonucleotide formyltransferase (GARFTase), it was of interest to dock all four analogues to explore the molecular basis of their activity against GARFTase. Molecular modeling studies were carried out using the X-ray crystal structure of human GARFTase bound to trifluoroacetyl-5,10-dideazaacyclic-5,6,7,8-tetrahydrofolic acid.[10] Docked poses of 10-(trifluoroacetyl)-5,10-dideazaacyclic-5,6,7,8-tetrahydrofolic acid, AGF23, AFG215, AGF234 and AGF263 were obtained. The pyrrolo[2,3-d]pyrimidine scaffold of all four analogs binds in the region occupied by the diaminopyrimidine ring in 10-CF$_3$CO-DDACTHF. The 2-NH$_2$, 3-NH and 7-NH of all four analogs interact with the same amino acids as the corresponding groups of 10-CF$_3$CO-DDACTHF. The pyrrolo[2,3-d]pyrimidine scaffold of all four analogs forms hydrophobic interactions with Ile91 and Val143. The α-carboxylic acid of AFG23, AGF234 and AGF263 interact with Arg64, Arg90, and the backbone of Ile91, however the α-carboxylic acid of AGF215 does not show these interactions. The γ-carboxylic acid of all four analogs interact with a water molecule. The docking scores of the four analogs were in the order, AGF263<AGF23=AGF234<AGF215. These interactions and the number of low energy docked conformations explain, in part, the rank order of potent inhibition against KB tumor cells in Table 11 of the four analogs.

On the basis of the docking studies in FRα and GARFTase, it is apparent that the conformations of the phenyl glutamic acid side chain have completely different orientations for FRα and GARFTase binding indicating the necessity for flexibility in order to provide both FRα and GARFTase binding.

Discussion of Compounds of Section IV:

AGF215, AGF234 and AGF263 were compared to AGF23 as inhibitors of proliferation of engineered Chinese hamster ovary (CHO) cells expressing human PCFT (R2/PCFT4), FRα (RT16), or RFC (PC43-10). AGF215 and AGF263, like AGF23, were inactive toward PC43-10 cells. AGF234 showed low level of activity towards PC43-10 cells. AGF23, AGF263 and AGF234 showed modest level activity toward R2/PCFT4 cells (IC$_{50}$~200-800 nM), whereas AGF215 was inactive. Toward FRα-expressing RT16 cells, AGF23, AGF215 and AG23F4 were potently inhibitory with IC$_{50}$ values of 1-6 nM. AGF215 and AGF234, like AGF23, were highly potent toward KB tumor cells with IC$_{50}$ values of 0.77 to 1.9 nM respectively; however AGF263 showed exceptionally high potency toward KB tumor cells with an IC$_{50}$ value of 0.22 nM. AG263, AGF215 and AGF234 are potential analogs for further preclinical studies and analog design.

Part V:

Xenograft Model for Selected Compounds of this Invention: AG165 (also identified as "RP/AG/159-411" in the figures) in the NCIADR resistant tumor model:

On day 11 of the trial tumor volume of AG165 (75 mg/kg) treated mice was significantly smaller than that of PTX (10 mg/kg) treated mice p=0.0333.

On day 11 of the trial tumor volume of AG165 (75 mg/kg) treated mice was significantly smaller than that of control treated mice p=0.0003.

AG165 in MDS-MB-231 Xenograph Model:

On days 10 and 15 tumors treated with AG165 (75 mg/kg) were significantly smaller than those treated with control p<0.01 and p<0.0001, respectively.

AG165 in MDA-MB-435 Xenograph Model:

On days 9, 11 and 15 tumors treated with AG165 (75 mg/kg) were significantly smaller than those treated with control p<0.01 on days 9 and 11 p<0.0001 on day 15.

Figure 12:
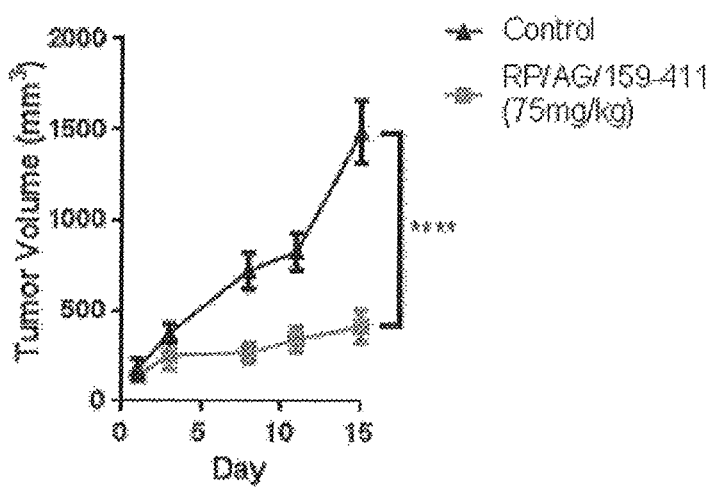
FIG. 12 shows the results of the MDA-MB-435 xenograft trial for AG165 (i.e. identified in FIG. 12 as RP/AG/159-411).

FIG. 12 shows the results of the MDA-MB-435 xenograft trial for AG165 (i.e. identified in FIG. 12 as RP/AG/159-411).

Figure 13:
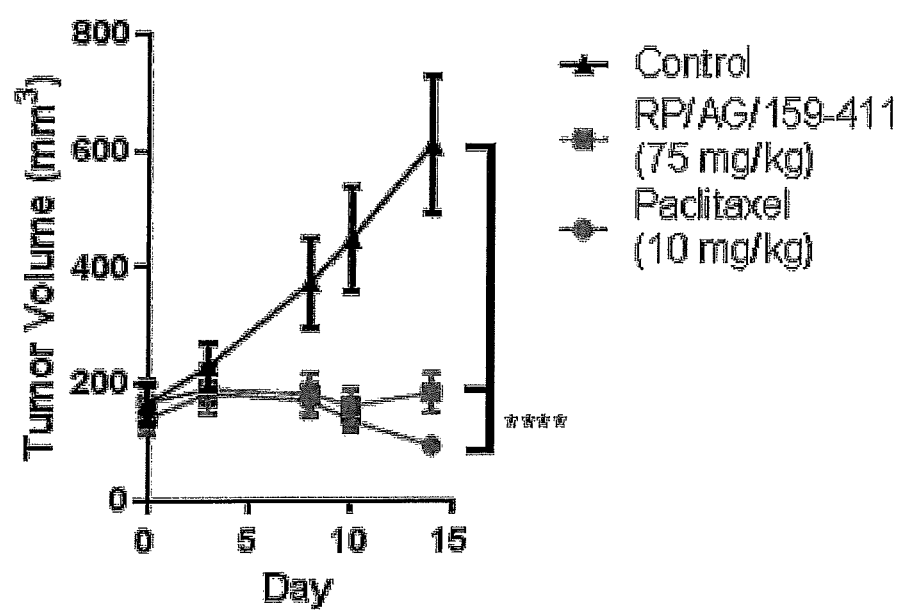
FIG. 13 shows the results of the MDA-MB-231 xenograft trial for AG165 (i.e. identified in FIG. 13 as RP/AG/159-411).

FIG. 13 shows the results of the MDA-MB-231 xenograft trial for AG165 (i.e. identified in FIG. 13 as RP/AG/159-411).

Figure 14:
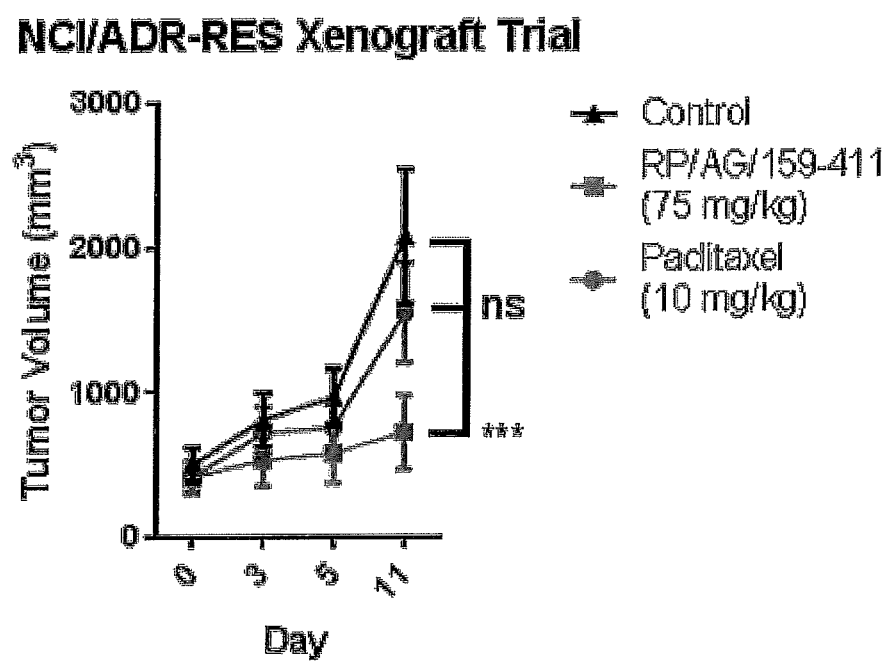
FIG. 14 shows the results of the NCI/ADR-RES xenograft trial for AG165 (i.e. identified in FIG. 14 as RP/AG/159-411), and comparison against paclitaxel (a known chemotherapeutic agent).

FIG. 14 shows the results of the NCI/ADR-RES xenograft trial for AG165 (i.e. identified in FIG. 14 as RP/AG/159-411), and comparison against paclitaxel (a known chemotherapeutic agent).

Figure 15:
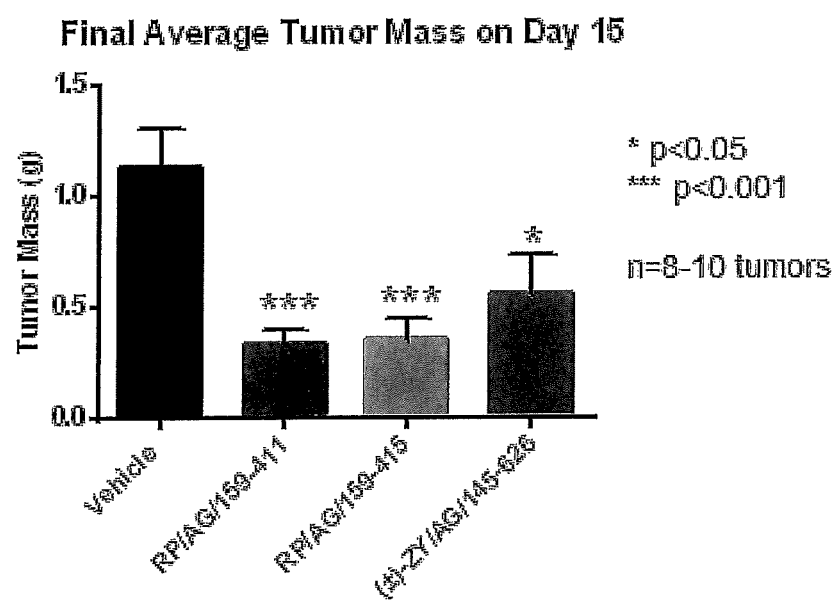
FIG. 15 shows in vivo antitumor effects in MDA-MB-435 xenograft model for AG165 (i.e. RP/AG/159-411), AG174 (identified as "RP/AG/159-415" in FIG. 15; see Formula VII for chemical structure thereof), and AG194 (identified as ZY/AG/145-626 in FIG. 15; see Formula VI for chemical structure thereof).

FIG. 15 shows in vivo antitumor effects in MDA-MB-435 xenograft model for AG165 (i.e. RP/AG/159-411), AG174 (identified as "RP/AG/159-415" in FIG. 15; see Formula VII for chemical structure thereof), and AG194 (identified as ZY/AG/145-626 in FIG. 15; see Formula VI for chemical structure thereof). MDA-MB-435 cells were implanted subcutaneously into both flanks of nude mice. Mice were treated with MTD and schedule using IP injections of 75 mg/kg. Cumulative dose=525 mg/kg for RP/AG/159-411 (AG165), 325 mg/kg for RP/AG/159-415 (AG174), and 450 mg/kg for ZY/AG/145-626 (AG194).

Figure 16:
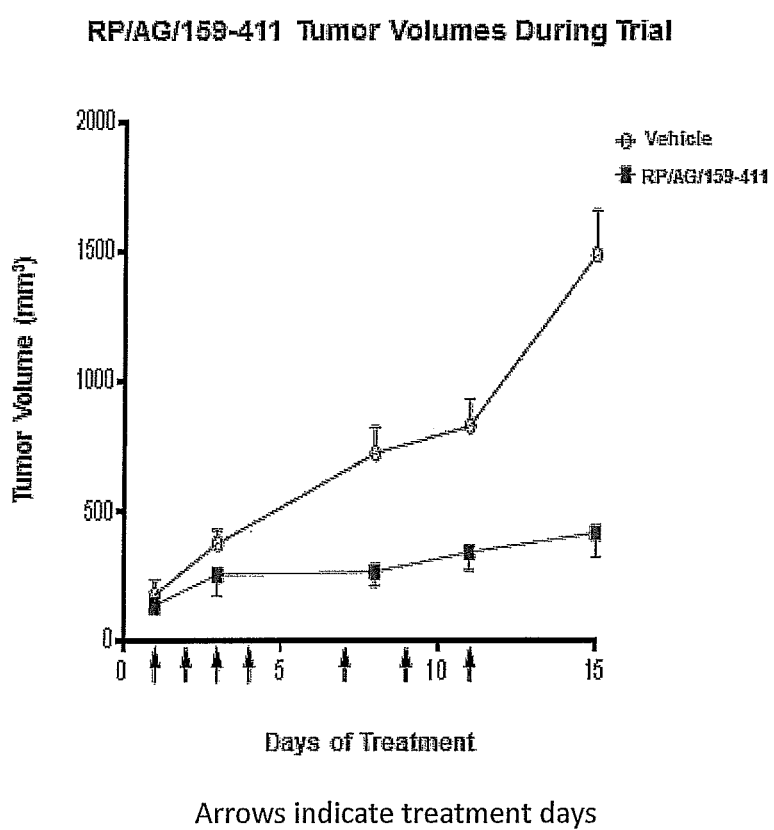
FIGS. 16 and 17 show tumor volumes and mass, respectively, during trial of RP/AG/159-415 (AG174) for in vivo antitumor effects in MDA-MB-435 xenograft model.
Figure 17:
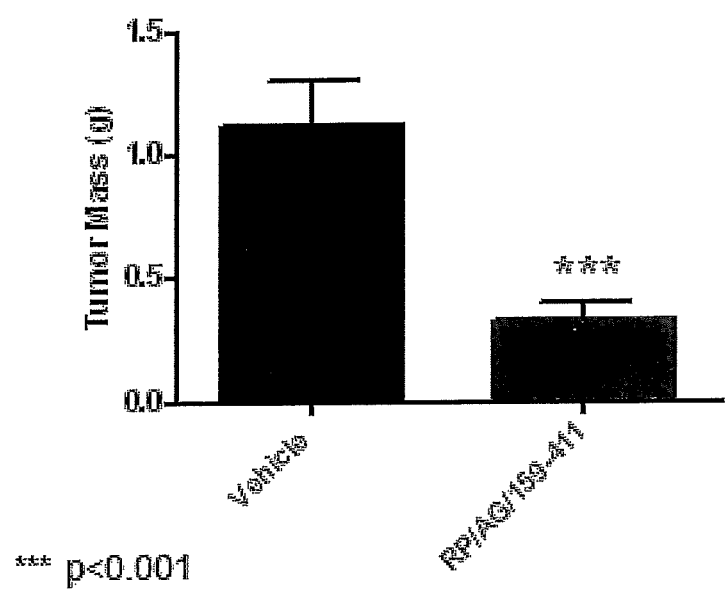

FIGS. 16 and 17 show tumor volumes and mass, respectively, during trial of RP/AG/159-415 (AG174) for in vivo antitumor effects in MDA-MB-435 xenograft model. MDA-MB-435 cells were implanted subcutaneously into both flanks of nude mice. Mice were treated each day indicted by arrows by IP injection of 75 mg/kg. Cumulative dose=525 mg/kg (n=8-10 tumors).

Figure 18:
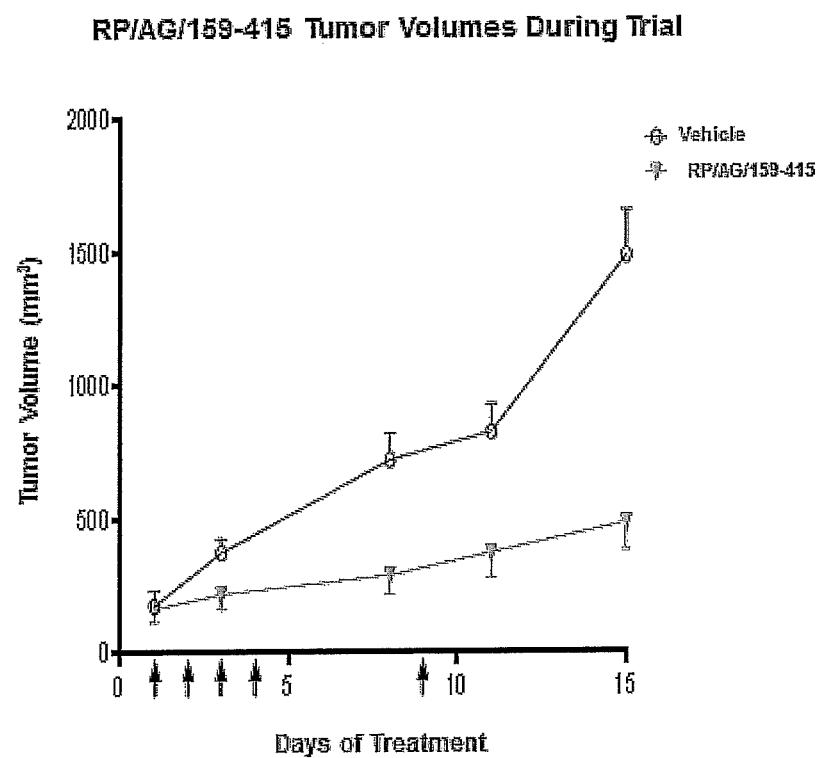
FIGS. 18 and 19 show tumor volumes and mass, respectively, during trial of RP/AG/159-411 (AG165) for in vivo antitumor effects in MDA-MB-435 xenograft model.
Figure 19:
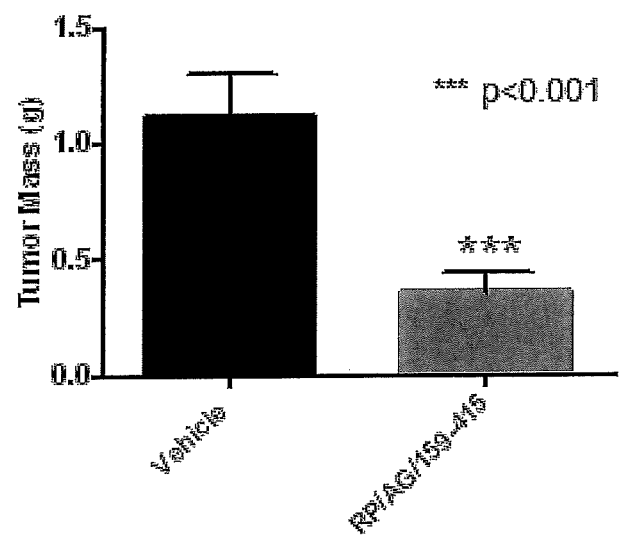

FIGS. 18 and 19 show tumor volumes and mass, respectively, during trial of RP/AG/159-411 (AG165) for in vivo antitumor effects in MDA-MB-435 xenograft model. MDA-MB-435 cells were implanted subcutaneously into both flanks of nude mice. Mice were treated each day indicted by arrows by IP injection of 75 mg/kg. Cumulative dose=375 mg/kg (n=8-10 tumors).

Figure 20:
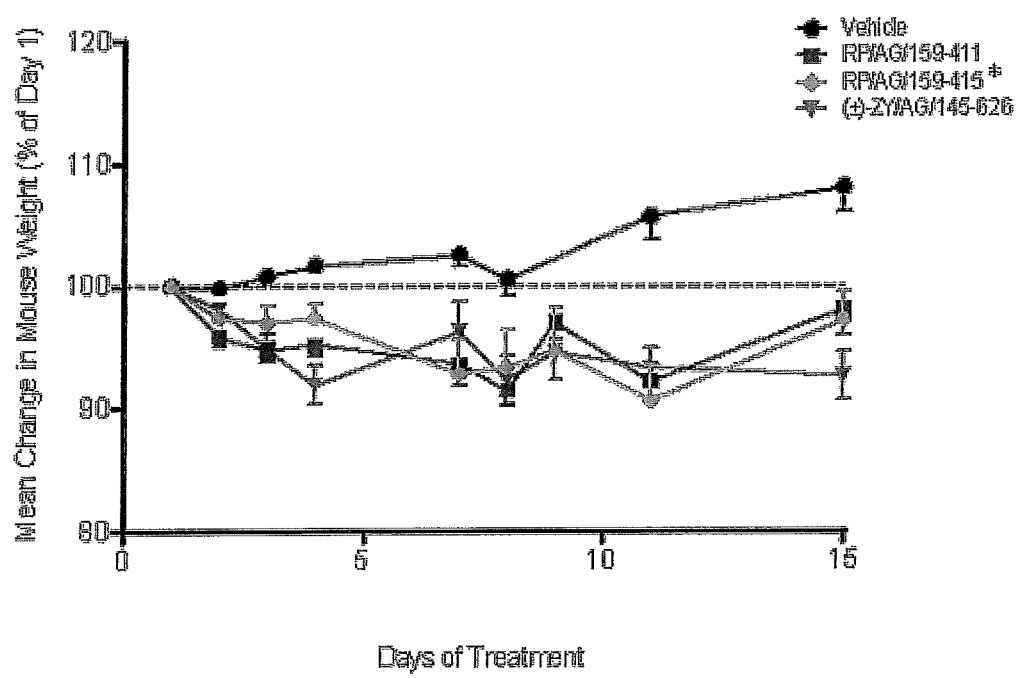
FIG. 20 shows percent change in weight during xenograft trial of AG165 and AG174.

FIG. 20 shows percent change in weight during xenograft trial of AG165 and AG174.

Figure 21:
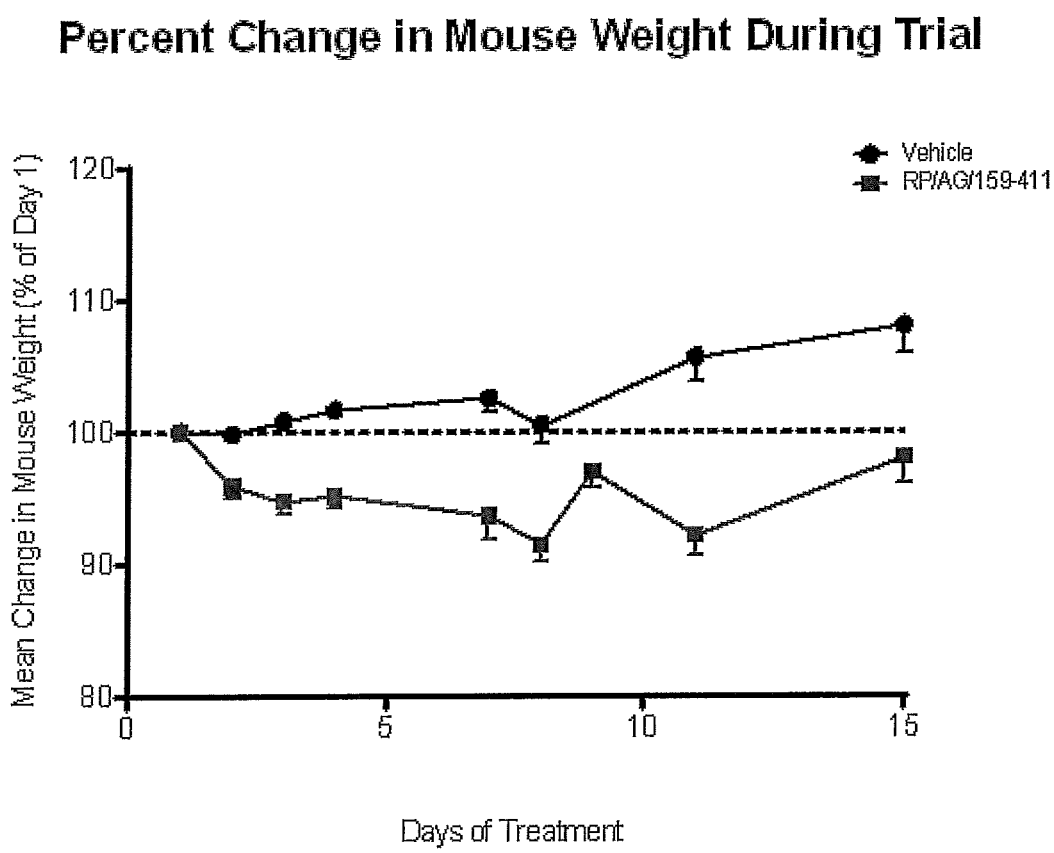
FIG. 21 shows percent change in weight during xenograft trial of AG165.

FIG. 21 shows percent change in weight during xenograft trial of AG165.

Figure 22:
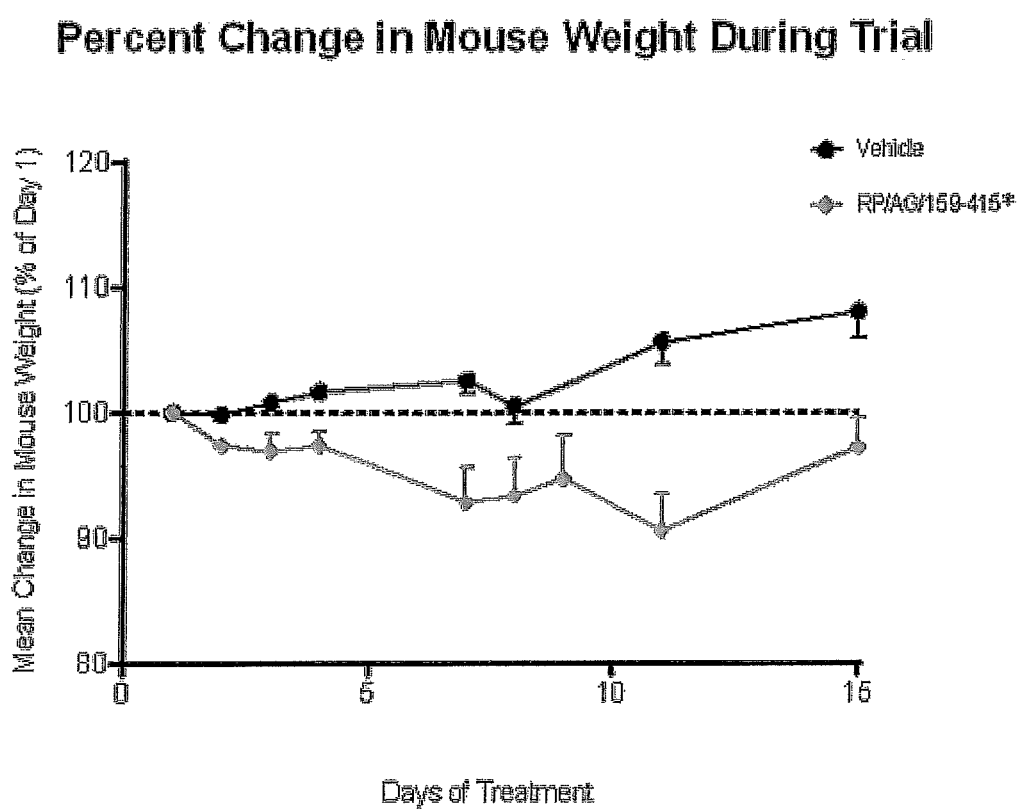
FIG. 22 shows percent change in weight during xenograft trial of AG174.

FIG. 22 shows percent change in weight during xenograft trial of AG174.

The results show that highly statistically significant (p<0.001) antitumor effects were observed with 2 compounds, RP/AG/159-415 (AG 174) and RP/AG/159-411 (AG 165). AG141 has unacceptable cumulative CNS toxicities that were not seen with RP/AG/159-411 (AG165). AG 141 caused severe seizures in two mice after they had lost more than 10% body weight, appeared to be cumulative dose effect. Stopped dosing after this. Other mice experience "dragging leg syndrome" suggestive of peripheral neuropathy. AG 165 caused recoverable weight loss with no evidence of effects on either central or peripheral nervous system.

SECTION I REFERENCES

1. Ma, J.; Waxman, D. J. Combination of antiangiogenesis with chemotherapy for more effective cancer treatment. *Mol. Cancer Ther.* 2008, 7, 3670-84.
2. Shibuya, M. Vascular endothelial growth factor and its receptor system: Physiological functions in angiogenesis and pathological roles in various diseases. *J. Biochem.* 2013, 153, 13-19.
3. www.clinicaltrials.gov
4. Matthews, D. J. G., M. E. Current challenges and future directions. In Targeting Protein Kinases for Cancer Therapy, Matthews, D. J. G., M. E., Ed. Wiley & Sons Inc: Hoboken, N.J., 2010; 623-663.
5. Hurvitz, S. A.; Dalenc, F.; Campone, M.; O'Regan, R. M.; Tjan-Heijnen, V. C.; Gligorov, J.; Llombart, A.; Jhangiani, H.; Mirshahidi, H. R.; Tan-Chiu, E.; Miao, S.; El-Hashimy, M.; Lincy, J.; Taran, T.; Soria, J. C.; Sahmoud, T.; Andre, F. Phase I study of everolimus plus weekly paclitaxel and trastuzumab in patients with metastatic breast cancer pretreated with trastuzumab. *J. Clin. Oncol.* 2010, 28, 5110-5115.
6. Holohan, C.; Van Schaeybroeck, S.; Longley, D. B.; Johnston, P. G., Cancer drug resistance: an evolving paradigm. *Nat. Rev. Cancer* 2013, 13, 714-726.
7. (a) Gangjee, A.; Zaware, N.; Raghavan, S.; Ihnat, M.; Shenoy, S.; Kisliuk, R. L. Single agents with designed combination chemotherapy potential: Synthesis and evaluation of substituted pyrimido[4,5-b]indoles as receptor tyrosine kinase and thymidylate synthase inhibitors and as antitumor agents. *J. Med. Chem.* 2010, 53, 1563-1578. (b) Gangjee, A.; Zhao, Y.; Ihnat, M. A.; Thorpe, J. E.; Bailey-Downs, L. C.; Kisliuk, R. L. Novel tricyclic indeno[2,1-d]pyrimidines with dual antiangiogenic and cytotoxic activities as potent antitumor agents. *Bioorg. Med. Chem.* 2012, 20, 4217-4225. (c) Gangjee, A.; Li, W.; Lin, L.; Zeng, Y.; Ihnat, M.; Warnke, L. A.; Green, D. W.; Cody, V.; Pace, J.; Queener, S. F. Design, synthesis, and X-ray crystal structures of 2,4-diaminofuro[2,3-d]pyrimidines as multireceptor tyrosine kinase and dihydrofolate reductase inhibitors. *Bioorg. Med. Chem.* 2009, 17, 7324-7336. (d) Gangjee, A.; Zeng, Y.; Ihnat, M.; Warnke, L. A.; Green, D. W.; Kisliuk, R. L.; Lin, F.-T. Novel 5-substituted, 2,4-diaminofuro[2,3-d]pyrimidines as multireceptor tyrosine kinase and dihydrofolate reductase inhibitors with antiangiogenic and antitumor activity. *Bioorg. Med. Chem.* 2005, 13, 5475-5491. (e) Gangjee, A.; Pavana, R. K.; Ihnat, M.; Thorpe, J.; Disch, B.; Nastain, A.; Bailey-Downs, L.; Hamel, E.; Bai, R. *ACS Med. Chem. Lett.* 2014, 5, 480-484.
8. Gangjee, A.; Pavana, R. K.; Li, W.; Hamel, E.; Westbrook, C.; Mooberry, S. L. *Pharm. Res.* 2012, 29, 3033-3039.
9. Gangjee, A.; Pavana, R. K.; Gentile, T.; Bai, R.; Hamel, E.; Ihnat, M. A.; Risinger, A. L.; Mooberry, S. L. Steric induced conformational restriction: Design, synthesis, and biological evaluation of novel pyrrolo[3,2-d]pyrimidines as water soluble antitubulin agents with antiangiogenic and antitumor potential. Abstracts of Papers, 246th ACS National Meeting & Exposition, Indianapolis, Ind., United States, Sep. 8-12, 2013.

SECTION II REFERENCES

1. Matesanz, R.; Trigili, C.; Rodriguez-Salarichs, J.; Zanardi, I.; Pera, B.; Nogales, A.; Fang, W. S.; Jimenez-Barbero, J.; Canales, A.; Barasoain, I.; Ojima, I.; Diaz, J. F., Taxanes with high potency inducing tubulin assembly overcome tumoural cell resistances. *Bioorganic & medicinal chemistry* 2014, 22, 5078-90.
2. Liu, Y. M.; Chen, H. L.; Lee, H. Y.; Liou, J. P., Tubulin inhibitors: a patent review. *Expert opinion on therapeutic patents* 2014, 24, 69-88.
3. Zhao, Z.; Castagnoli, N.; Ricaurte, G. A.; Steele, T.; Martello, M., Synthesis and neurotoxicological evaluation of putative metabolites of the serotonergic neurotoxin 2-(methylamino)-1-[3,4-(methylenedioxy)phenyl]propane [(methylenedioxy)methamphetamine]. *Chemical Research in Toxicology* 1992, 5, 89-94.
4. Staack, R. F.; Theobald, D. S.; Paul, L. D.; Springer, D.; Kraemer, T.; Maurer, H. H., In vivo metabolism of the new designer drug 1-(4-methoxyphenyl)piperazine (MeOPP) in rat and identification of the human cytochrome P450 enzymes responsible for the major metabolic step. *Xenobiotica; the fate of foreign compounds in biological systems* 2004, 34, 179-92.
5. Suzuki, Y.; Jin, C.; Iwase, T.; Yazawa, I., β-III Tubulin Fragments Inhibit α-Synuclein Accumulation in Models of Multiple System Atrophy. *J. Biol. Chem.* 2014, 289, 24374-24382.
6. Tsourlakis, M. C.; Weigand, P.; Grupp, K.; Kluth, M.; Steurer, S.; Schlomm, T.; Graefen, M.; Huland, H.; Salomon, G.; Steuber, T.; Wilczak, W.; Sirma, H.; Simon, R.; Sauter, G.; Minner, S.; Quaas, A., βIII-Tubulin Overexpression Is an Independent Predictor of Prostate Cancer Progression Tightly Linked to ERG Fusion Status and PTEN Deletion. *Am. J. Pathol.* 2014, 184, 609-617.
7. Zhao, Z. Y.; Castagnoli, N., Jr.; Ricaurte, G. A.; Steele, T.; Martello, M., Synthesis and neurotoxicological evaluation of putative metabolites of the serotonergic neurotoxin 2-(methylamino)-1-[3,4-(methylenedioxy)phenyl] propane [(methylenedioxy)methamphetamine]. *Chemical research in toxicology* 1992, 5, 89-94.
8. mol_rmsd, *Scientific Vector Language (SVL)* source code provided by Chemical Computing Group Inc., 1010 Sherbooke St. West, Suite #910, Montreal, QC, Canada, H3A 2R7, 2012.

SECTION III REFERENCES

1. Komlodi-Pasztor, E.; Sackett D.; Wilkerson J.; Fojo T. Mitosis is not a key target of microtubule agents in patient tumors. *Nat. Rev. Clin. Oncol.* 2011, 8, 244-250.
2. Dumontet, C.; Jordan, M. A. Microtubule-binding agents: A dynamic field of cancer therapeutics. *Nat. Rev. Drug Discov.* 2010, 9, 790-803.
3. Jordan, M. A.; Kamath, K. How do microtubule-targeted drugs work? An overview. *Curr. Cancer Drug Targets* 2007, 7, 730-742.
4. Correia, J. J.; Lobert, S. Physiochemical aspects of tubulin-interacting antimitotic drugs. *Current Pharmaceutical Design* 2001, 7, 1213-1228.
5. Patterson, D. M.; Rustin, G. J. S. Combretastatin A-4 phosphate: Vascular disrupting agent: Oncolytic: Treatment of age-related macular degeneration. *Drugs Future* 2007, 32, 1025-1032.
6. Fojo, A. T.; Menefee, M. Microtubule targeting agents: Basic mechanisms of multidrug resistance (MDR). *Semin. Oncol.* 2005, 32, S3-S8
7. McCarroll, J. A.; Gan, P. P.; Liu, M.; Kavallaris, M. βIII-Tubulin is a multifunctional protein involved in drug sensitivity and tumorigenesis in non-small cell lung cancer. *Cancer Res.* 2010, 70, 4995-5003.
8. Gangjee, A.; Mohan, R.; Bai R.; Hamel, E. Design, synthesis and biological evaluation of substituted monocyclic pyrimidines with cytotoxic antitubulin activities as antitumor agents. From Abstracts of Papers, 246th American Chemical Society National Meeting and Exposition (ACS), Indianapolis, Ind., Sep. 8-12, 2013. Abstract No: 311

SECTION IV REFERENCES

1. Matherly, L. H.; Goldman, I. D. *Vitam. Horm.* 2003, 66, 403-456.
2. Matherly, L. H.; Hou, Z.; Deng, Y. *Cancer Metastasis Rev.* 2007, 26, 111-128.
3. Zhao, R.; Matherly, L. H.; Goldman, I. D. *Expert Rev. Mol. Med.* 2009, 11, No. e4.
4. Salazar, M. D.; Ratnam, M. *Cancer Metastasis Rev.* 2007, 26, 141-152.
5. Elnakat, H.; Ratnam, M. *Adv. Drug Delivery* 2004, 56, 1067-1084.
6. Goldman, I. D. et al. *Cell* 2006, 127, 917-928.
7. Zhao, R.; Goldman, I. D. *Cancer Metastasis Rev.* 2007, 26, 129-139.
8. Deng, Y.; Wang, Y.; Cherian, C.; Hou, Zhanjun; Buck, S. A.; Matherly, L. H.; Gangjee, A. *J. Med. Chem.* 2008, 51, 5052-5063.
9. Chen, C.; Ke, J.; Zhou, X. E.; Yi, W.; Brunzelle, J. S.; Li, J.; Yong, E.-L.; Xu, H. E.; Melcher, K. *Nature* 2013, 500 (7463), 486-489.
10. Zhang, Y.; Desharnais, J.; Marsilje, T. H.; Li, C.; Hedrick, M. P.; Gooljarsingh, L. T.; Tavassoli, A.; Benkovic, S. J.; Olson, A. J.; Boger, D. L.; Wilson, I. A. *Biochemistry* 2003, 42 (20), 6043-6056.

I claim:
1. A compound of Formula II, and salts thereof:

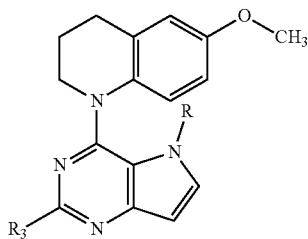

wherein R is hydrogen or an alkyl group having from one to ten carbon atoms, and wherein $R_3$ is a halogen.

2. A compound of Formula II, and salt thereof, of claim 1 wherein said halogen is one selected from the group consisting of chlorine, bromine, fluorine, and iodine.

3. The compound of Formula II, and salt thereof, of claim 1 wherein R is a hydrogen.

4. A compound of Formula II, and salt thereof, of claim 2 or 3 wherein $R_3$ is a chlorine.

5. A compound of Formula II, and salt thereof, of claim 1, wherein R is a methyl group.

6. The compound of Formula II, and salt thereof, of claim 5, wherein $R_3$ is chlorine.

7. A pharmaceutical composition comprising a compound of Formula II and a pharmaceutically acceptable salt thereof:

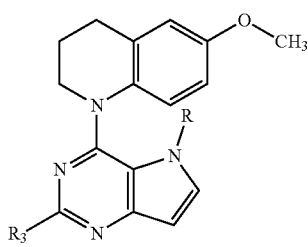

wherein R is hydrogen or an alkyl group having from one to ten carbon atoms, and wherein $R_3$ is a halogen.

* * * * *